United States Patent
Henrichs et al.

(10) Patent No.: US 10,621,192 B2
(45) Date of Patent: *Apr. 14, 2020

(54) METHOD AND APPARATUS FOR ACCELERATED FORMAT TRANSLATION OF DATA IN A DELIMITED DATA FORMAT

(71) Applicant: IP Reservoir, LLC, Creve Coeur, MO (US)

(72) Inventors: Michael John Henrichs, Eureka, MO (US); Joseph M. Lancaster, St. Louis, MO (US); Roger Dean Chamberlain, St. Louis, MO (US); Jason R. White, Manchester, MO (US); Kevin Brian Sprague, Clayton, MO (US); Terry Tidwell, St. Louis, MO (US)

(73) Assignee: IP Resevoir, LLC, St. Louis, MO (US)

( * ) Notice: Subject to any disclaimer, the term of this patent is extended or adjusted under 35 U.S.C. 154(b) by 0 days.

This patent is subject to a terminal disclaimer.

(21) Appl. No.: 15/489,065

(22) Filed: Apr. 17, 2017

(65) Prior Publication Data
US 2017/0220655 A1 Aug. 3, 2017

Related U.S. Application Data

(63) Continuation of application No. 14/060,313, filed on Oct. 22, 2013, now Pat. No. 9,633,093.

(60) Provisional application No. 61/717,496, filed on Oct. 23, 2012.

(51) Int. Cl.
*G06F 16/25* (2019.01)
*G06F 16/28* (2019.01)

(52) U.S. Cl.
CPC .......... *G06F 16/254* (2019.01); *G06F 16/258* (2019.01); *G06F 16/283* (2019.01)

(58) Field of Classification Search
USPC ........................................................ 707/602
See application file for complete search history.

(56) References Cited

U.S. PATENT DOCUMENTS

| 3,601,808 A | 8/1971 | Vlack |
| 3,611,314 A | 10/1971 | Pritchard, Jr. et al. |
| 3,729,712 A | 4/1973 | Glassman |

(Continued)

FOREIGN PATENT DOCUMENTS

| EP | 0573991 | 12/1993 |
| EP | 0880088 | 11/1996 |

(Continued)

OTHER PUBLICATIONS

Dharmapurikar, "Fast and Scalable Pattern Matching for Content Filtering", ACM, ANCS 05, 2005, pp. 183-192.

(Continued)

*Primary Examiner* — Tamara T Kyle
*Assistant Examiner* — Raheem Hoffler
(74) *Attorney, Agent, or Firm* — Thompson Coburn LLP

(57) ABSTRACT

Various methods and apparatuses are described for performing high speed format translations of incoming data, where the incoming data is arranged in a delimited data format. As an example, the data in the delimited data format can be translated to a fixed field format using pipelined operations. A reconfigurable logic device can be used in exemplary embodiments as a platform for the format translation.

40 Claims, 23 Drawing Sheets

(56) References Cited

U.S. PATENT DOCUMENTS

| | | |
|---|---|---|
| 3,824,375 A | 7/1974 | Gross et al. |
| 3,848,235 A | 11/1974 | Lewis et al. |
| 3,906,455 A | 9/1975 | Houston et al. |
| 4,081,607 A | 3/1978 | Vitols et al. |
| 4,298,898 A | 11/1981 | Cardot |
| 4,314,356 A | 2/1982 | Scarbrough |
| 4,385,393 A | 5/1983 | Chaure et al. |
| 4,464,718 A | 8/1984 | Dixon et al. |
| 4,550,436 A | 10/1985 | Freeman et al. |
| 4,823,306 A | 4/1989 | Barbic et al. |
| 4,941,178 A | 7/1990 | Chuang |
| 5,023,910 A | 6/1991 | Thomson |
| 5,050,075 A | 9/1991 | Herman et al. |
| 5,101,424 A | 3/1992 | Clayton et al. |
| 5,140,692 A | 8/1992 | Morita |
| 5,161,103 A | 11/1992 | Kosaka et al. |
| 5,163,131 A | 11/1992 | Row et al. |
| 5,179,626 A | 1/1993 | Thomson |
| 5,226,165 A | 7/1993 | Martin |
| 5,243,655 A | 9/1993 | Wang |
| 5,249,292 A | 9/1993 | Chiappa |
| 5,255,136 A | 10/1993 | Machado et al. |
| 5,263,156 A | 11/1993 | Bowen et al. |
| 5,265,065 A | 11/1993 | Turtle |
| 5,267,148 A | 11/1993 | Kosaka et al. |
| 5,313,560 A | 5/1994 | Maruoka et al. |
| 5,319,776 A | 6/1994 | Hile et al. |
| 5,327,521 A | 7/1994 | Savic et al. |
| 5,339,411 A | 8/1994 | Heaton, Jr. |
| 5,347,634 A | 9/1994 | Herrell et al. |
| 5,371,794 A | 12/1994 | Diffie et al. |
| 5,388,259 A | 2/1995 | Fleischman et al. |
| 5,396,253 A | 3/1995 | Chia |
| 5,404,411 A | 4/1995 | Banton et al. |
| 5,404,488 A | 4/1995 | Kerrigan et al. |
| 5,418,951 A | 5/1995 | Damashek |
| 5,421,028 A | 5/1995 | Swanson |
| 5,432,822 A | 7/1995 | Kaewell, Jr. |
| 5,440,723 A | 8/1995 | Arnold et al. |
| 5,461,712 A | 10/1995 | Chelstowski et al. |
| 5,463,701 A | 10/1995 | Kantner, Jr. et al. |
| 5,465,353 A | 11/1995 | Hull et al. |
| 5,481,735 A | 1/1996 | Mortensen et al. |
| 5,488,725 A | 1/1996 | Turtle et al. |
| 5,497,488 A | 3/1996 | Akizawa et al. |
| 5,517,642 A | 5/1996 | Bezek et al. |
| 5,544,352 A | 8/1996 | Egger |
| 5,546,578 A | 8/1996 | Takada et al. |
| 5,651,125 A | 7/1997 | Witt et al. |
| 5,687,297 A | 11/1997 | Coonan et al. |
| 5,701,464 A | 12/1997 | Aucsmith |
| 5,704,060 A | 12/1997 | Del Monte |
| 5,712,942 A | 1/1998 | Jennings et al. |
| 5,721,898 A | 2/1998 | Beardsley et al. |
| 5,740,466 A | 4/1998 | Geldman et al. |
| 5,774,835 A | 6/1998 | Ozawa et al. |
| 5,774,839 A | 6/1998 | Shlomot |
| 5,781,772 A | 7/1998 | Wilkinson, III et al. |
| 5,781,921 A | 7/1998 | Nichols |
| 5,805,832 A | 9/1998 | Brown et al. |
| 5,813,000 A | 9/1998 | Furlani |
| 5,819,273 A | 10/1998 | Vora et al. |
| 5,819,290 A | 10/1998 | Fujita et al. |
| 5,826,075 A | 10/1998 | Bealkowski et al. |
| 5,864,738 A | 1/1999 | Kessler et al. |
| 5,870,730 A | 2/1999 | Furuya et al. |
| 5,886,701 A | 3/1999 | Chauvin et al. |
| 5,913,211 A | 6/1999 | Nitta |
| 5,930,753 A | 7/1999 | Potamianos et al. |
| 5,943,421 A | 8/1999 | Grabon |
| 5,943,429 A | 8/1999 | Händel |
| 5,978,801 A | 11/1999 | Yuasa |
| 5,987,432 A | 11/1999 | Zusman et al. |
| 5,991,881 A | 11/1999 | Conklin et al. |
| 5,995,963 A | 11/1999 | Nanba et al. |
| 6,006,264 A | 12/1999 | Colby et al. |
| 6,023,760 A | 2/2000 | Karttunen |
| 6,028,939 A | 2/2000 | Yin |
| 6,044,407 A | 3/2000 | Jones et al. |
| 6,058,391 A | 5/2000 | Gardner |
| 6,064,739 A | 5/2000 | Davis |
| 6,067,569 A | 5/2000 | Khaki et al. |
| 6,070,172 A | 5/2000 | Lowe |
| 6,073,160 A | 6/2000 | Grantham et al. |
| 6,105,067 A | 8/2000 | Batra |
| 6,134,551 A | 10/2000 | Aucsmith |
| 6,138,176 A | 10/2000 | McDonald et al. |
| RE36,946 E | 11/2000 | Diffie et al. |
| 6,147,976 A | 11/2000 | Shand et al. |
| 6,169,969 B1 | 1/2001 | Cohen |
| 6,175,874 B1 | 1/2001 | Imai et al. |
| 6,226,676 B1 | 5/2001 | Crump et al. |
| 6,236,980 B1 | 5/2001 | Reese |
| 6,279,113 B1 | 8/2001 | Vaidya |
| 6,317,795 B1 | 11/2001 | Malkin et al. |
| 6,336,150 B1 | 1/2002 | Ellis et al. |
| 6,339,819 B1 | 1/2002 | Huppenthal et al. |
| 6,370,645 B1 | 4/2002 | Lee et al. |
| 6,377,942 B1 | 4/2002 | Hinsley et al. |
| 6,381,242 B1 | 4/2002 | Maher, III et al. |
| 6,389,532 B1 | 5/2002 | Gupta et al. |
| 6,397,259 B1 | 5/2002 | Lincke et al. |
| 6,397,335 B1 | 5/2002 | Franczek et al. |
| 6,412,000 B1 | 6/2002 | Riddle et al. |
| 6,430,272 B1 | 8/2002 | Maruyama et al. |
| 6,456,632 B1 | 9/2002 | Baum et al. |
| 6,463,474 B1 | 10/2002 | Fuh et al. |
| 6,499,107 B1 | 12/2002 | Gleichauf et al. |
| 6,502,133 B1 | 12/2002 | Baulier et al. |
| 6,535,868 B1 | 3/2003 | Galeazzi et al. |
| 6,564,263 B1 | 5/2003 | Bergman et al. |
| 6,578,147 B1 | 6/2003 | Shanklin et al. |
| 6,625,150 B1 | 9/2003 | Yu |
| 6,704,816 B1 | 3/2004 | Burke |
| 6,711,558 B1 | 3/2004 | Indeck et al. |
| 6,765,918 B1 | 7/2004 | Dixon et al. |
| 6,772,345 B1 | 8/2004 | Shetty |
| 6,785,677 B1 | 8/2004 | Fritchman |
| 6,804,667 B1 | 10/2004 | Martin |
| 6,807,156 B1 | 10/2004 | Veres et al. |
| 6,839,686 B1 | 1/2005 | Galant |
| 6,850,906 B1 | 2/2005 | Chadha et al. |
| 6,870,837 B2 | 3/2005 | Ho et al. |
| 6,877,044 B2 | 4/2005 | Lo et al. |
| 6,886,103 B1 | 4/2005 | Brustoloni et al. |
| 6,901,461 B2 | 5/2005 | Bennett |
| 6,931,408 B2 | 8/2005 | Adams et al. |
| 6,931,545 B1 | 8/2005 | Ta et al. |
| 6,944,168 B2 | 9/2005 | Paatela et al. |
| 6,978,223 B2 | 12/2005 | Milliken |
| 6,980,976 B2 | 12/2005 | Alpha et al. |
| 6,981,054 B1 | 12/2005 | Krishna |
| 7,007,208 B1 * | 2/2006 | Hibbert ............... H04L 1/24 341/51 |
| 7,019,674 B2 | 3/2006 | Cadambi et al. |
| 7,046,848 B1 | 5/2006 | Olcott |
| 7,093,023 B2 | 8/2006 | Lockwood et al. |
| 7,127,424 B2 | 10/2006 | Kemp, II et al. |
| 7,139,743 B2 | 11/2006 | Indeck et al. |
| 7,149,715 B2 | 12/2006 | Browne et al. |
| 7,167,980 B2 | 1/2007 | Chiu |
| 7,177,833 B1 | 2/2007 | Marynowski et al. |
| 7,181,437 B2 | 2/2007 | Indeck et al. |
| 7,181,608 B2 | 2/2007 | Fallon et al. |
| 7,222,114 B1 | 5/2007 | Chan et al. |
| 7,224,185 B2 | 5/2007 | Campbell et al. |
| 7,225,188 B1 | 5/2007 | Gai et al. |
| 7,251,629 B1 | 7/2007 | Marynowski et al. |
| 7,287,037 B2 | 10/2007 | An et al. |
| 7,305,383 B1 | 12/2007 | Kubesh et al. |
| 7,305,391 B2 | 12/2007 | Wyschogrod et al. |
| 7,363,277 B1 | 4/2008 | Dutta et al. |
| 7,386,564 B2 | 6/2008 | Abdo et al. |
| 7,408,932 B2 | 8/2008 | Kounavis et al. |

(56) References Cited

U.S. PATENT DOCUMENTS

| | | |
|---|---|---|
| 7,411,957 B2 | 8/2008 | Stacy et al. |
| 7,420,931 B2 | 9/2008 | Nanda et al. |
| 7,433,878 B2 * | 10/2008 | Mika .................. G06Q 40/00 |
| 7,444,515 B2 | 10/2008 | Dharmapurikar et al. |
| 7,454,418 B1 | 11/2008 | Wang |
| 7,457,834 B2 | 11/2008 | Jung et al. |
| 7,461,064 B2 | 12/2008 | Fontoura et al. |
| 7,467,155 B2 | 12/2008 | McCool et al. |
| 7,478,431 B1 | 1/2009 | Nachenberg |
| 7,480,253 B1 | 1/2009 | Allan |
| 7,487,327 B1 | 2/2009 | Chang et al. |
| 7,496,108 B2 | 2/2009 | Biran et al. |
| 7,552,107 B2 | 6/2009 | Indeck et al. |
| 7,558,925 B2 | 7/2009 | Bouchard et al. |
| 7,565,525 B2 | 7/2009 | Vorbach et al. |
| 7,636,703 B2 | 12/2009 | Taylor |
| 7,660,793 B2 | 2/2010 | Indeck et al. |
| 7,680,790 B2 | 3/2010 | Indeck et al. |
| 7,685,121 B2 | 3/2010 | Brown et al. |
| 7,685,254 B2 | 3/2010 | Pandya |
| 7,701,945 B2 | 4/2010 | Roesch et al. |
| 7,702,629 B2 | 4/2010 | Cytron et al. |
| 7,783,862 B2 | 8/2010 | Cameron |
| 7,805,392 B1 | 9/2010 | Steele et al. |
| 7,840,482 B2 | 11/2010 | Singla et al. |
| 7,917,299 B2 | 3/2011 | Buhler et al. |
| 7,921,046 B2 | 4/2011 | Parsons et al. |
| 7,945,528 B2 | 5/2011 | Cytron et al. |
| 7,949,650 B2 | 5/2011 | Indeck et al. |
| 8,095,508 B2 | 1/2012 | Chamberlain et al. |
| 8,275,885 B2 | 9/2012 | Hu et al. |
| 8,374,986 B2 | 2/2013 | Indeck et al. |
| 8,407,588 B1 | 3/2013 | Hu et al. |
| 8,620,881 B2 | 12/2013 | Chamberlain et al. |
| 8,751,452 B2 | 6/2014 | Chamberlain et al. |
| 8,768,888 B2 | 7/2014 | Chamberlain et al. |
| 9,176,775 B2 | 11/2015 | Chamberlain et al. |
| 9,633,093 B2 | 4/2017 | Henrichs et al. |
| 9,633,097 B2 | 4/2017 | Tidwell et al. |
| 10,102,260 B2 | 10/2018 | Lancaster et al. |
| 10,158,377 B2 | 12/2018 | Indeck et al. |
| 2001/0013048 A1 | 8/2001 | Imbert de Tremiolles et al. |
| 2001/0014093 A1 | 8/2001 | Yoda et al. |
| 2001/0052038 A1 | 12/2001 | Fallon et al. |
| 2001/0056547 A1 | 12/2001 | Dixon |
| 2002/0031125 A1 | 3/2002 | Sato |
| 2002/0069370 A1 | 6/2002 | Mack |
| 2002/0091691 A1 | 7/2002 | Sharp |
| 2002/0095512 A1 | 7/2002 | Rana et al. |
| 2002/0103663 A1 | 8/2002 | Bankier et al. |
| 2002/0105911 A1 | 8/2002 | Pruthi et al. |
| 2002/0129140 A1 | 9/2002 | Peled et al. |
| 2002/0150248 A1 | 10/2002 | Kovacevic |
| 2002/0162025 A1 | 10/2002 | Sutton et al. |
| 2002/0166063 A1 | 11/2002 | Lachman et al. |
| 2003/0009693 A1 | 1/2003 | Brock et al. |
| 2003/0014521 A1 | 1/2003 | Elson et al. |
| 2003/0014662 A1 | 1/2003 | Gupta et al. |
| 2003/0018630 A1 | 1/2003 | Indeck et al. |
| 2003/0023876 A1 | 1/2003 | Bardsley et al. |
| 2003/0037037 A1 | 2/2003 | Adams et al. |
| 2003/0043805 A1 | 3/2003 | Graham et al. |
| 2003/0051043 A1 | 3/2003 | Wyschogrod et al. |
| 2003/0065943 A1 | 4/2003 | Geis et al. |
| 2003/0074582 A1 | 4/2003 | Patel et al. |
| 2003/0110229 A1 | 6/2003 | Kulig et al. |
| 2003/0115485 A1 | 6/2003 | Milliken |
| 2003/0163715 A1 | 8/2003 | Wong |
| 2003/0169877 A1 | 9/2003 | Liu et al. |
| 2003/0177253 A1 | 9/2003 | Schuehler et al. |
| 2003/0221013 A1 | 11/2003 | Lockwood et al. |
| 2004/0019703 A1 | 1/2004 | Burton |
| 2004/0028047 A1 | 2/2004 | Hou et al. |
| 2004/0049596 A1 | 3/2004 | Schuehler et al. |
| 2004/0054924 A1 | 3/2004 | Chuah et al. |
| 2004/0064737 A1 | 4/2004 | Milliken et al. |
| 2004/0100977 A1 | 5/2004 | Suzuki et al. |
| 2004/0111632 A1 | 6/2004 | Halperin |
| 2004/0117645 A1 | 6/2004 | Okuda et al. |
| 2004/0153813 A1 | 8/2004 | Swoboda |
| 2004/0162826 A1 | 8/2004 | Wyschogrod et al. |
| 2004/0177340 A1 | 9/2004 | Hsu et al. |
| 2004/0186804 A1 | 9/2004 | Chakraborty et al. |
| 2004/0186814 A1 | 9/2004 | Chalermkraivuth et al. |
| 2004/0196905 A1 | 10/2004 | Yamane et al. |
| 2004/0199448 A1 | 10/2004 | Chalermkraivuth et al. |
| 2004/0205149 A1 | 10/2004 | Dillon et al. |
| 2005/0005145 A1 | 1/2005 | Teixeira |
| 2005/0086520 A1 | 4/2005 | Dharmapurikar et al. |
| 2005/0131790 A1 | 6/2005 | Benzschawel et al. |
| 2005/0175010 A1 | 8/2005 | Wilson et al. |
| 2005/0187844 A1 | 8/2005 | Chalermkraivuth et al. |
| 2005/0187845 A1 | 8/2005 | Eklund et al. |
| 2005/0187846 A1 | 8/2005 | Subbu et al. |
| 2005/0187847 A1 | 8/2005 | Bonissone et al. |
| 2005/0187848 A1 | 8/2005 | Bonissone et al. |
| 2005/0187849 A1 | 8/2005 | Bollapragada et al. |
| 2005/0187974 A1 | 8/2005 | Gong |
| 2005/0195832 A1 | 9/2005 | Dharmapurikar et al. |
| 2005/0229254 A1 | 10/2005 | Singh et al. |
| 2006/0020715 A1 | 1/2006 | Jungck |
| 2006/0031154 A1 | 2/2006 | Noviello et al. |
| 2006/0031156 A1 | 2/2006 | Noviello et al. |
| 2006/0031263 A1 | 2/2006 | Arrouye et al. |
| 2006/0031737 A1 | 2/2006 | Chugg et al. |
| 2006/0036693 A1 | 2/2006 | Hulten et al. |
| 2006/0047636 A1 | 3/2006 | Mohania et al. |
| 2006/0053295 A1 | 3/2006 | Madhusudan et al. |
| 2006/0059213 A1 | 3/2006 | Evoy |
| 2006/0129745 A1 | 6/2006 | Thiel et al. |
| 2006/0198375 A1 | 9/2006 | Baik et al. |
| 2006/0242123 A1 | 10/2006 | Williams, Jr. |
| 2006/0259417 A1 | 11/2006 | Marynowski et al. |
| 2006/0269148 A1 | 11/2006 | Farber et al. |
| 2006/0294059 A1 | 12/2006 | Chamberlain et al. |
| 2007/0011175 A1 | 1/2007 | Langseth et al. |
| 2007/0011183 A1 | 1/2007 | Langseth et al. |
| 2007/0011317 A1 | 1/2007 | Brandyburg et al. |
| 2007/0011687 A1 | 1/2007 | Ilik et al. |
| 2007/0061594 A1 | 3/2007 | Ginter et al. |
| 2007/0067108 A1 | 3/2007 | Buhler et al. |
| 2007/0067481 A1 | 3/2007 | Sharma et al. |
| 2007/0078837 A1 | 4/2007 | Indeck et al. |
| 2007/0094199 A1 | 4/2007 | Deshpande et al. |
| 2007/0112748 A1 | 5/2007 | Angell et al. |
| 2007/0112837 A1 | 5/2007 | Houh et al. |
| 2007/0118500 A1 | 5/2007 | Indeck et al. |
| 2007/0130140 A1 | 6/2007 | Cytron et al. |
| 2007/0156574 A1 | 7/2007 | Marynowski et al. |
| 2007/0156669 A1 | 7/2007 | Marchisio et al. |
| 2007/0174841 A1 * | 7/2007 | Chamberlain ........ G06F 9/3879 719/310 |
| 2007/0179935 A1 | 8/2007 | Lee et al. |
| 2007/0209068 A1 | 9/2007 | Ansari et al. |
| 2007/0237327 A1 | 10/2007 | Taylor et al. |
| 2007/0244859 A1 | 10/2007 | Trippe et al. |
| 2007/0260602 A1 | 11/2007 | Taylor |
| 2007/0277036 A1 | 11/2007 | Chamberlain et al. |
| 2007/0294157 A1 | 12/2007 | Singla et al. |
| 2008/0005062 A1 | 1/2008 | Gupta et al. |
| 2008/0021874 A1 | 1/2008 | Dahl et al. |
| 2008/0030383 A1 * | 2/2008 | Cameron ............ G06F 17/277 341/55 |
| 2008/0040657 A1 * | 2/2008 | Kuznetsov ........... G06F 17/227 715/234 |
| 2008/0077582 A1 | 3/2008 | Reed |
| 2008/0084573 A1 | 4/2008 | Horowitz et al. |
| 2008/0086274 A1 | 4/2008 | Chamberlain et al. |
| 2008/0104542 A1 | 5/2008 | Cohen et al. |
| 2008/0109413 A1 | 5/2008 | Indeck et al. |
| 2008/0114724 A1 | 5/2008 | Indeck et al. |
| 2008/0114725 A1 | 5/2008 | Indeck et al. |
| 2008/0114760 A1 | 5/2008 | Indeck et al. |
| 2008/0126320 A1 | 5/2008 | Indeck et al. |

(56) References Cited

U.S. PATENT DOCUMENTS

| | | | |
|---|---|---|---|
| 2008/0133453 A1 | 6/2008 | Indeck et al. | |
| 2008/0133519 A1 | 6/2008 | Indeck et al. | |
| 2008/0243675 A1 | 10/2008 | Parsons et al. | |
| 2008/0307435 A1 | 12/2008 | Rehman | |
| 2009/0007197 A1 | 1/2009 | Turner | |
| 2009/0182683 A1 | 7/2009 | Taylor et al. | |
| 2009/0262741 A1 | 10/2009 | Jungck et al. | |
| 2009/0287628 A1 | 11/2009 | Indeck et al. | |
| 2009/0300054 A1 | 12/2009 | Fisher et al. | |
| 2010/0094858 A1 | 4/2010 | Indeck et al. | |
| 2010/0145902 A1 | 6/2010 | Boyan et al. | |
| 2010/0198850 A1 | 8/2010 | Cytron et al. | |
| 2010/0284532 A1 | 11/2010 | Burnett et al. | |
| 2011/0040701 A1 | 2/2011 | Singla et al. | |
| 2011/0078109 A1 | 3/2011 | Griggs et al. | |
| 2011/0123021 A1 | 5/2011 | Tepper | |
| 2012/0114119 A1* | 5/2012 | Ahuja ............... | H04L 63/0853 380/44 |
| 2012/0311411 A1 | 12/2012 | Kirkpatrick | |
| 2013/0151458 A1 | 6/2013 | Indeck et al. | |
| 2014/0114908 A1 | 4/2014 | Henrichs et al. | |
| 2014/0114929 A1 | 4/2014 | Henrichs et al. | |
| 2014/0279864 A1 | 9/2014 | Lopyrev et al. | |
| 2015/0310077 A1 | 10/2015 | Lancaster et al. | |
| 2015/0310078 A1 | 10/2015 | Lancaster et al. | |
| 2015/0310087 A1 | 10/2015 | Tidwell et al. | |
| 2017/0123866 A1 | 5/2017 | Indeck et al. | |
| 2017/0124166 A1 | 5/2017 | Thomas et al. | |
| 2019/0079984 A1 | 3/2019 | Lancaster et al. | |
| 2019/0108177 A1 | 4/2019 | Henrichs et al. | |
| 2019/0123764 A1 | 4/2019 | Indeck et al. | |

FOREIGN PATENT DOCUMENTS

| | | |
|---|---|---|
| EP | 0851358 A | 7/1998 |
| EP | 0887723 | 12/1998 |
| EP | 0911738 A | 4/1999 |
| JP | 02136900 A | 5/1990 |
| JP | 03014075 A | 1/1991 |
| JP | 09145544 A | 6/1997 |
| JP | 2000286715 A | 10/2000 |
| JP | 2001357048 A | 12/2001 |
| JP | 2002101089 A | 4/2002 |
| WO | 199010910 | 9/1990 |
| WO | 1994/09443 A1 | 4/1994 |
| WO | 199737735 | 10/1997 |
| WO | 199905814 | 2/1999 |
| WO | 2000041136 A1 | 7/2000 |
| WO | 2001022425 A | 3/2001 |
| WO | 2001039577 | 6/2001 |
| WO | 2001061913 | 8/2001 |
| WO | 2001080082 A2 | 10/2001 |
| WO | 2001080558 | 10/2001 |
| WO | 2002061525 | 8/2002 |
| WO | 2002082271 | 10/2002 |
| WO | 2003100650 | 4/2003 |
| WO | 2003036845 | 5/2003 |
| WO | 2004017604 | 2/2004 |
| WO | 2004042560 A | 5/2004 |
| WO | 2004042561 A | 5/2004 |
| WO | 2004042562 | 5/2004 |
| WO | 2004042574 A | 5/2004 |
| WO | 2005017708 A | 2/2005 |
| WO | 2005026925 | 3/2005 |
| WO | 2005048134 A | 5/2005 |
| WO | 2006023948 | 3/2006 |
| WO | 2006096324 | 9/2006 |
| WO | 2007064685 | 6/2007 |
| WO | 2007087507 | 8/2007 |
| WO | 2008063973 | 5/2008 |
| WO | 2008063974 | 5/2008 |
| WO | 2009029842 | 3/2009 |
| WO | 2009089467 A2 | 7/2009 |
| WO | 2009140363 A1 | 11/2009 |
| WO | 2014/066416 A2 | 5/2014 |
| WO | 2015/164639 | 10/2015 |

OTHER PUBLICATIONS

Ebeling et al., "RaPiD—Reconfigurable Pipelined Datapath", University of Washington, Dept. of Computer Science and Engineering, Sep. 23, 1996, Seattle, WA.

Exegy Inc., "Exegy and HyperFeed to Unveil Exelerate Tp at Sia Conference", Release Date: Jun. 20, 2006, downloaded from http://news.thomasnet.com/companystory/488004 on Jun. 19, 2007, 4 pages.

Exegy Inc., "First Exegy Ticker Plant Deployed", Release Date: Oct. 17, 2006, downloaded from http://news.thomasnet.com/companystory/496530 on Jun. 19, 2007, 5 pages.

Extended European Search Report for EP Application 13849798.7 dated Jul. 14, 2016.

Feldman, "High Frequency Traders Get Boost From FPGA Acceleration", Jun. 8, 2007, downloaded from http://www.hpcwire.com/hpc.1600113.html on Jun. 19, 2007, 4 pages.

Feldmann, "BLT: Bi-Layer Tracing of HTTP and TCP/IP", AT&T Labs-Research, Florham Park, NJ, USA.

Fernandez, "Template Matching of Binary Targets in Grey-Scale Images: A Nonparametric Approach", Pattern Recognition, 1997, pp. 1175-1182, vol. 30, No. 7.

Forgy, "RETE: A Fast Algorithm for the Many Pattern/Many Object Pattern Matching Problem", Artificial Intelligence, 1982, pp. 17-37, vol. 19.

Franklin et al., "An Architecture for Fast Processing of Large Unstructured Data Sets." Proc. of 22nd Int'l Conf. on Computer Design, Oct. 2004, pp. 280-287.

Franklin et al., "Assisting Network Intrusion Detection with Reconfigurable Hardware", Symposium on Field-Programmable Custom Computing Machines (FCCM 2002), Apr. 2002, Napa, California.

Fu et al., "The FPX KCPSM Module: an Embedded, Reconfigurable Active Processing Module for the Field Programmable Port Extender (FPX)", Washington University, Department of Computer Science, Technical Report WUCS-01-14, Jul. 2001.

Gavrila et al., "Multi-feature Hierarchical Template Matching Using Distance Transforms", IEEE, 08/16-20/1998, vol. 1, pp. 439-444.

Google Search Results Page for "field programmable gate array financial calculation stock market" over dates of Jan. 1, 1990-May 21, 2002, 1 page.

Guerdoux-Jamet et al., "Systolic Filter for Fast DNA Similarity Search", IEEE, 1995, pp. 145-156.

Gunther et al., "Assessing Document Relevance with Run-Time Reconfigurable Machines", FPGAs for Custom Computing Machines, 1996, Proceedings, IEEE Symposium on, pp. 10-17, Napa Valley, CA, Apr. 17, 1996.

Gupta et al., "High-Speed Implementations of Rule-Based Systems," ACM Transactions on Computer Systems, May 1989, pp. 119-146, vol. 7, Issue 2.

Gupta et al., "Packet Classification on Multiple Fields", Computer Systems Laboratory, Stanford University, Stanford, CA.

Gupta et al., "PMM: A Parallel Architecture for Production Systems," Proceedings of the IEEE, Apr. 1992, pp. 693-696, vol. 2.

Gurtov, "Effect of Delays on TCP Performance", Cellular Systems Development, Sonera Corporation, online at http://cs.helsinki.fi/u/gurtov/papers/pwc01.pdf.

Gyang, "NCBI BLASTN Stage 1 in Reconfigurable Hardware," Technical Report WUCSE-2005-30, Aug. 2004, Department of Computer Science and Engineering, Washington University, St. Louis, MO.

Halaas et al., "A Recursive MISD Architecture for Pattern Matching", IEEE Transactions on Very Large Scale Integration, vol. 12, No. 7, pp. 727-734, Jul. 2004.

Harris, "Pete's Blog: Can FPGAs Overcome the FUD?", Low-Latency.com, May 14, 2007, URL: http://www.a-teamgroup.com/article/pete-blog-can-fpgas-overcome-the-fud/.

(56) References Cited

OTHER PUBLICATIONS

Hauck et al., "Software Technologies for Reconfigurable Systems", Northwestern University, Dept. of ECE, Technical Report, 1996.
Hayes, "Computer Architecture and Organization", Second Edition, 1988, pp. 448-459, McGraw-Hill, Inc.
Herbordt et al., "Single Pass, BLAST-Like, Approximate String Matching on FPGAs", 14th Annual IEEE Symposium on Field-Programmable Custom Computing Machines (FCCM'06), Apr. 2006, pp. 1-10, IEEE.
Hezel et al., "FPGA-Based Template Matching Using Distance Transforms", Proceedings of the 10th Annual IEEE Symposium on Field-Programmable Custom Computing Machines, Apr. 22, 2002, pp. 89-97, IEEE Computer Society, USA.
Hirsch, "Tech Predictions for 2008", Reconfigurable Computing, Jan. 16, 2008, URL: http://fpgacomputing.blogspot.com/2008_01_01_archive.html.
Hollaar, "Hardware Systems for Text Information Retrieval", Proceedings of the Sixth Annual International ACM Sigir Conference on Research and Development in Information Retrieval, Jun. 6-8, 1983, pp. 3-9, Baltimore, Maryland, USA.
Hutchings et al., "Assisting Network Intrusion Detection with Reconfigurable Hardware", FCCM 2002: 10th Annual IEEE Symposium on Field-Programmable Custom Computing Machines, 2002.
International Preliminary Report on Patentability (Chapter I) for PCT/US2015/027348 dated Nov. 3, 2016.
International Search Report and Written Opinion for PCT/US2013/066224 dated Jan. 16, 2014.
Jacobson et al., "RFC 1072: TCP Extensions for Long-Delay Paths", Oct. 1988.
Jacobson et al., "tcpdump—dump traffic on a network", Jun. 30, 1997, online at www.cse.cuhk.edu.hk/~cslui/CEG4430/tcpdump.ps.gz.
Johnson et al., "Pattern Matching in Reconfigurable Logic for Packet Classification", College of Computing, Georgia Institute of Technology, Atlanta, GA.
Jones et al., "A Probabilistic Model of Information Retrieval: Development and Status", Information Processing and Management, Aug. 1998, 76 pages.
Keutzer et al., "A Survey of Programmable Platforms—Network Proc", University of California—Berkeley, pp. 1-29.
Koloniari et al., "Content-Based Routing of Path Queries in Peer-to-Peer Systems", pp. 1-19, E. Bertino et al. (Eds.): EDBT 2004, LNCS 2992, pp. 29-47, 2004, copyright by Springer-Verlag, Germany.
Krishnamurthy et al, "Biosequence Similarity Search on the Mercury System", Proceedings of the 15th IEEE International Conference on Application-Specific Systems, Architectures, and Processors (ASAP04), Sep. 2004, pp. 365-375.
Kulig et al., "System and Method for Controlling Transmission of Data Packets Over an Information Network", pending U.S. Patent Application.
Lancaster et al., "Acceleration of Ungapped Extension in Mercury BLAST", Seventh (7th) Workshop on Media and Streaming Processors, Nov. 12, 2005, Thirty-Eighth (38th) International Symposium on Microarchitecture (MICRO-38), Barcelona, Spain.
Li et al., "Large-Scale IP Traceback in High-Speed Internet: Practical Techniques and Theoretical Foundation", Proceedings of the 2004 IEEE Symposium on Security and Privacy, 2004, pp. 1-15.
Lin et al., "Real-Time Image Template Matching Based on Systolic Array Processor", International Journal of Electronics; Dec. 1, 1992; pp. 1165-1176; vol. 73, No. 6; London, Great Britain.
Lockwood et al, "Field Programmable Port Extender (FPX) for Distributed Routing and Queuing", ACM International Symposium on Field Programmable Gate Arrays (FPGA 2000), Monterey, CA, Feb. 2000, pp. 137-144.
Lockwood et al., "Hello, World: A Simple Application for the Field Programmable Port Extender (FPX)", Washington University, Department of Computer Science, Technical Report WUCS-00-12, Jul. 11, 2000.
Lockwood et al., "Parallel FPGA Programming over Backplane Chassis", Washington University, Department of Computer Science, Technical Report WUCS-00-11, Jun. 12, 2000.
Lockwood et al., "Reprogrammable Network Packet Processing on the Field Programmable Port Extender (FPX)", ACM International Symposium on Field Programmable Gate Arrays (FPGA 2001), Monterey, CA, Feb. 2001, pp. 87-93.
Lockwood, "An Open Platform for Development of Network Processing Modules in Reprogrammable Hardware", IEC DesignCon 2001, Santa Clara, CA, Jan. 2001, Paper WB-19.
Lockwood, "Building Networks with Reprogrammable Hardware", Field Programmable Port Extender: Jan. 2002 Gigabit Workshop Tutorial, Washington University, St. Louis, MO, Jan. 3-4, 2002.
Lockwood, "Evolvable Internet Hardware Platforms", NASA/DoD Workshop on Evolvable Hardware (EHW'01), Long Beach, CA, Jul. 12-14, 2001, pp. 271-279.
Office Action for U.S. Appl. No. 14/060,339 dated Nov. 2, 2017.
Office Action for U.S. Appl. No. 14/694,580 dated Sep. 8, 2017.
Office Action for U.S. Appl. No. 14/694,595 dated Nov. 30, 2017.
Office Action for U.S. Appl. No. 15/404,794 dated Jan. 25, 2018.
Prosecution History for U.S. Appl. No. 14/060,313, filed Oct. 22, 2013 (Henrichs et al.).
"A Reconfigurable Computing Model for Biological Research Application of Smith-Waterman Analysis to Bacterial Genomes" A White Paper Prepared by Star Bridge Systems, Inc. [retrieved Dec. 12, 2006]. Retrieved from the Internet: (URL: http://www.starbridgesystems.com/resources/whitepapers/Smith%20 Waterman%20Whitepaper.pdf.
"ACTIV Financial Announces Hardware Based Market Data Feed Processing Strategy", for Release on Apr. 2, 2007, 2 pages.
"ACTIV Financial Delivers Accelerated Market Data Feed", Apr. 6, 2007, byline of Apr. 2, 2007, downloaded from http://hpcwire.com/hpc.1346816.html on Jun. 19, 2007, 3 pages.
"DRC, Exegy Announce Joint Development Agreement", Jun. 8, 2007, byline of Jun. 4, 2007; downloaded from http://www.hpcwire.com/hpc/1595644.html on Jun. 19, 2007, 3 pages.
"Lucent Technologies Delivers "PayloadPlus" Network Processors for Programmable, MultiProtocol, OC-48c Processing", Lucent Technologies Press Release, downloaded from http://www.lucent.com/press/1000/0010320.meb.html on Mar. 21, 2002.
"Overview, Field Programmable Port Extender", Jan. 2002 Gigabit Workshop Tutorial, Washington University, St. Louis, MO, Jan. 3-4, 2002, pp. 1-4.
"Payload Plus™ Agere System Interface", Agere Systems Product Brief, Jun. 2001, downloaded from Internet, Jan. 2002, pp. 1-6.
"RFC793: Transmission Control Protocol, Darpa Internet Program, Protocol Specification", Sep. 1981.
"Technology Overview", Data Search Systems Incorporated, downloaded from the http://www.datasearchsystems.com/tech.htm on Apr. 19, 2004.
"The Field-Programmable Port Extender (FPX)", downloaded from http://www.arl.wustl.edu/arl/ in Mar. 2002.
Aldwairi et al., "Configurable String Matching Hardware for Speeding up Intrusion Detection", SIRARCH Comput. Archit. News, vol. 33, No. 1, pp. 99-107, Mar. 2005.
Amanuma et al., "A FPGA Architecture for High Speed Computation", Proceedings of 60th Convention Architecture, Software Science, Engineering, Mar. 14, 2000, pp. 1-163-1-164, Information Processing Society, Japan.
Amer-Yahia et al., "XQuery 1.0 and XPath 2.0 Full-Text 1.0", W3C Working Draft, http://www.w3.org/TR/query-full-text/, May 18, 2007—parts 1-4.
Anerousis et al., "Using the AT&T Labs PacketScope for Internet Measurement, Design, and Performance Analysis", Network and Distributed Systems Research Laboratory, AT&T Labs-Research, Florham, Park, NJ, Oct. 1997.
Anonymous, "Method for Allocating Computer Disk Space to a File of Known Size", IBM Technical Disclosure Bulletin, vol. 27, No. 10B, Mar. 1, 1985, New York.
Arnold et al., "The Splash 2 Processor and Applications", Proceedings 1993 IEEE International Conference on Computer Design: VLSI in Computers and Processors (ICCD '93), Oct. 3, 1993, pp. 482-485, IEEE Computer Society, Cambridge, MA USA.

(56) References Cited

OTHER PUBLICATIONS

Artan et al., "Multi-packet Signature Detection using Prefix Bloom Filters", 2005, IEEE, pp. 1811-1816.

Asami et al., "Improvement of DES Key Search on FPGA-Based Parallel Machine "RASH"", Proceedings of Information Processing Society, Aug. 15, 2000, pp. 50-57, vol. 41, No. SIG5 (HPS1), Japan.

Baboescu et al., "Scalable Packet Classification," SIGCOMM'01, Aug. 27-31, 2001, pp. 199-210, San Diego, California, USA; http://www.ecse.rpi.edu/homepages/shivkuma/teaching/sp2001/readings/baboescu-pkt-classification.pdf.

Baer, "Computer Systems Architecture", 1980, pp. 262-265; Computer Science Press, Potomac, Maryland.

Baeza-Yates et al., "New and Faster Filters for Multiple Approximate String Matching", Random Structures and Algorithms (RSA), Jan. 2002, pp. 23-49, vol. 20, No. 1.

Baker et al., "High-throughput Linked-Pattern Matching for Intrusion Detection Systems", ANCS 2005: Proceedings of the 2005 Symposium on Architecture for Networking and Communications Systems, pp. 193-202, ACM Press, 2005.

Barone-Adesi et al., "Efficient Analytic Approximation of American Option Values", Journal of Finance, vol. 42, No. 2 (Jun. 1987), pp. 301-320.

Behrens et al., "BLASTN Redundancy Filter in Reprogrammable Hardware," Final Project Submission, Fall 2003, Department of Computer Science and Engineering, Washington University.

Berk, "JLex: A lexical analyzer generator for Java™", downloaded from http://www.cs.princeton.edu/~appel/modern/java/Jlex/ in Jan. 2002, pp. 1-18.

Bloom, "Space/Time Trade-offs in Hash Coding With Allowable Errors", Communications of the ACM, Jul. 1970, pp. 422-426, vol. 13, No. 7, Computer Usage Company, Newton Upper Falls, Massachusetts, USA.

Braun et al., "Layered Protocol Wrappers for Internet Packet Processing in Reconfigurable Hardware", Proceedings of Hot Interconnects 9 (Hotl-9) Stanford, CA, Aug. 22-24, 2001, pp. 93-98.

Braun et al., "Protocol Wrappers for Layered Network Packet Processing in Reconfigurable Hardware", IEEE Micro, Jan.-Feb. 2002, pp. 66-74.

Brodie et al., "Dynamic Reconfigurable Computing", in Proc. of 9th Military and Aerospace Programmable Logic Devices International Conference, Sep. 2006.

Cavnar et al., "N-Gram-Based Text Categorization", Proceedings of SDAIR-94, 3rd Annual Symposium on Document Analysis and Information Retrieval, Las Vegas, pp. 161-175, 1994.

Chamberlain et al., "Achieving Real Data Throughput for an FPGA Co-Processor on Commodity Server Platforms", Proc. of 1st Workshop on Building Block Engine Architectures for Computers and Networks, Oct. 2004, Boston, MA.

Chamberlain et al., "The Mercury System: Embedding Computation Into Disk Drives", 7th High Performance Embedded Computing Workshop, Sep. 2003, Boston, MA.

Chaney et al., "Design of a Gigabit ATM Switch", Washington University, St. Louis.

Cho et al., "Deep Packet Filter with Dedicated Logic and Read Only Memories", 12th Annual IEEE Symposium on Field-Programmable Custom Computing Machines, Apr. 2004.

Cho, "A Fast Regular Expression Indexing Engine", Proc. of 18th Int'l Conv. On Data Engineering, 2001, pp. 1-12.

Choi et al., "Design of a Flexible Open Platform for High Performance Active Networks", Allerton Conference, 1999, Champaign, IL.

Clark et al., "Scalable Pattern Matching for High Speed Networks", Proceedings of the 12th Annual IEEE Symposium on Field-Programmable Custom Computing Machines, 2004; FCCM 2004, Apr. 20-23, 2004; pp. 249-257; IEEE Computer Society; Cambridge, MA USA.

Cloutier et al., "VIP: An FPGA-Based Processor for Image Processing and Neural Networks", Proceedings of Fifth International Conference on Microelectronics for Neural Networks, Feb. 12, 1996, pp. 330-336, Los Alamitos, California.

Compton et al., "Configurable Computing: A Survey of Systems and Software", Technical Report, Northwestern University, Dept. of ECE, 1999.

Compton et al., "Reconfigurable Computing: a Survey of Systems and Software", Technical Report, Northwestern University, Dept. of ECE, 1999, presented by Yi-Gang Tai.

Cong et al., "An Optional Technology Mapping Algorithm for Delay Optimization in Lookup-Table Based FPGA Designs", IEEE, 1992, pp. 48-53.

Crosman, "Who Will Cure Your Data Latency?", Storage & Servers, Jun. 20, 2007, URL: http://www.networkcomputing.com/article/printFullArticleSrc.jhtml?article ID=199905630.

Cuppu and Jacob, "Organizational Design Trade-Offs at the DRAM, Memory Bus and Memory Controller Level: Initial Results," Technical Report UMB-SCA-1999-2, Univ. of Maryland Systems & Computer Architecture Group, Nov. 1999, pp. 1-10.

Denoyer et al., "HMM-based Passage Models for Document Classification and Ranking", Proceedings of ECIR-01, 23rd European Colloquim Information Retrieval Research, Darmstatd, DE, pp. 126-135, 2001.

Department of Computer Science & Engineering; "Technical Reports"; Publication (http://cse.seas.wustl.edu/Research/Publications.asp); Dec. 17, 2007; pp. 1-26; Washington University in St. Louis.

Dharmapurikar et al., "Deep Packet Inspection Using Parallel Bloom Filters," IEEE Micro, Jan.-Feb. 2004, vol. 24, Issue: 1, pp. 52-61.

Dharmapurikar et al., "Deep Packet Inspection Using Parallel Bloom Filters," Symposium on High Performance Interconnects (Hotl), Stanford, California, 2003, pp. 44-51.

Dharmapurikar et al., "Design and Implementation of a String Matching System for Network Intrusion Detection using FPGA-based Bloom Filters", Proc. of 12th Annual IEEE Symposium on Field Programmable Custom Computing Machines, 2004, pp. 1-10.

Dharmapurikar et al., "Longest Prefix Matching Using Bloom Filters," SIGCOMM, 2003, pp. 201-212.

Dharmapurikar et al., "Robust TCP Stream Reassembly in the Presence of Adversaries", Proc. of the 14th Conference on USENIX Security Symposium—vol. 14, 16 pages, Baltimore, MD, 2005; http://www.icir.org/vern/papers/TcpReassembly/TCPReassembly.pdf.

Lockwood, "Hardware Laboratory Configuration", Field Programmable Port Extender: Jan. 2002 Gigabit Workshop Tutorial, Washington University, St. Louis, MO, Jan. 3-4, 2002.

Lockwood, "Introduction", Field Programmable Port Extender: Jan. 2002 Gigabit Workshop Tutorial, Washington University, St. Louis, MO, Jan. 3-4, 2002.

Lockwood, "Platform and Methodology for Teaching Design of Hardware Modules in Internet Routers and Firewalls", IEEE Computer Society International Conference on Microelectronic Systems Education (MSE'2001), Las Vegas, NV, Jun. 17-18, 2001, pp. 56-57.

Lockwood, "Protocol Processing on the FPX", Field Programmable Port Extender: January 2002 Gigabit Workshop Tutorial, Washington University, St. Louis, MO, Jan. 3-4, 2002.

Lockwood, "Simulation and Synthesis", Field Programmable Port Extender: Jan. 2002 Gigabit Workshop Tutorial, Washington University, St. Louis, MO, Jan. 3-4, 2002.

Lockwood, "Simulation of the Hello World Application for the Field-Programmable Port Extender (FPX)", Washington University, Applied Research Lab, Spring 2001 Gigabits Kits Workshop.

Madhusudan, "Design of a System for Real-Time Worm Detection", Hot Interconnects, pp. 77-83, Stanford, CA, Aug. 2004, found at http://www.hoti.org/hoti12/program/papers/2004/paper4.2.pdf.

Madhusudan, "Design of a System for Real-Time Worm Detection", Power Point Presentation in Support of Master's Thesis, Washington Univ., Dept. of Computer Science and Engineering, St. Louis, MO, Aug. 2004.

Mao et al., "Cluster-based Online Monitoring System of Web Traffic", Dept. of Computer Science and Technology, Tsinghua Univ., Bejing, 100084 P.R. China.

Mosanya et al., "A Fpga-Based Hardware Implementation of Generalized Profile Search Using Online Arithmetic", ACM/SIGDA

(56) References Cited

OTHER PUBLICATIONS

International Symposium on Field Programmable Gate Arrays (FPGA '99), Feb. 21-23, 1999, pp. 101-111, Monterey, CA, USA.

Moscola et al., "FPGrep and FPSed: Regular Expression Search and Substitution for Packet Streaming in Field Programmable Hardware", Dept. of Computer Science, Applied Research Lab, Washington University, Jan. 8, 2002, unpublished, pp. 1-19, St. Louis, MO.

Moscola et al., "FPSed: A Streaming Content Search-and-Replace Module for an Internet Firewall", Proc. of Hot Interconnects, 11th Symposium on High Performance Interconnects, pp. 122-129, Aug. 20, 2003.

Moscola, "FPGrep and FPSed: Packet Payload Processors for Managing the Flow of Digital Content on Local Area Networks and the Internet", Master's Thesis, Sever Institute of Technology, Washington University, St. Louis, MO, Aug. 2003.

Navarro, "A Guided Tour to Approximate String Matching", ACM Computing Surveys, vol. 33, No. 1, Mar. 2001, pp. 31-88.

Necker et al., "TCP-Stream Reassembly and State Tracking in Hardware", School of Electrical and Computer Engineering, Georgia Institute of Technology, Atlanta, GA.

Niewczas et al., "A Pattern Matching Algorithm for Verification and Analysis of Very Large IC Layouts", ACM, Apr. 1998, pp. 129-134.

Nunez et al., "The X-MatchLITE FPGA-Based Data Compressor", Euromicro Conference 1999, Proceedings, Italy, Sep. 8-10, 1999, pp. 126-132, Los Alamitos, CA.

Nwodoh et al., "A Processing System for Real-Time Holographic Video Computation", Reconfigurable Technology: FPGAs for Computing and Application, Proceedings for the SPIE, Sep. 1999, Boston, pp. 129-140, vol. 3844.

Office Action for U.S. Appl. No. 14/060,339 dated Aug. 8, 2016.

Office Action for U.S. Appl. No. 14/694,622 dated Jun. 24, 2016.

Partial International Search Report for PCT/US03/15638 dated Feb. 3, 2004.

Prakash et al., "OC-3072 Packet Classification Using BDDs and Pipelined SRAMs", Department of Electrical and Computer Engineering, The University of Texas at Austin.

Pramanik et al., "A Hardware Pattern Matching Algorithm on a Dataflow"; Computer Journal; Jul. 1, 1985; pp. 264-269; vol. 28, No. 3; Oxford University Press, Surrey, Great Britain.

Prosecution History for U.S. Appl. No. 14/060,339, filed Oct. 22, 2013 (Henrichs et al.).

Prosecution History for U.S. Appl. No. 14/694,580, filed Apr. 23, 2015 (Lancaster et al.).

Prosecution History for U.S. Appl. No. 14/694,595, filed Apr. 23, 2015 (Lancaster et al.).

Prosecution History of U.S. Appl. No. 14/694,622, filed Apr. 23, 2015 (Tidwell et al.).

Ramakrishna et al., "A Performance Study of Hashing Functions for Hardware Applications", Int. Conf. on Computing and Information, May 1994, pp. 1621-1636, vol. 1, No. 1.

Ramakrishna et al., "Efficient Hardware Flashing Functions for High Performance Computers", IEEE Transactions on Computers, Dec. 1997, vol. 46, No. 12.

Ramesh et al., "Automatic Selection of Tuning Parameters for Feature Extraction Sequences", IEEE, Jun. 21-23, 1994, pp. 672-677.

Ratha et al., "Convolution on Splash 2", Proceedings of IEEE Symposium on FPGAS for Custom Computing Machines, Apr. 19, 1995, pp. 204-213, Los Alamitos, California.

Ratha et al., "FPGA-based coprocessor for text string extraction", IEEE, Sep. 11-13, 2000, pp. 217-221.

Roberts, "Internet Still Growing Dramatically Says Internet Founder", Press Release, Caspian Networks, Inc.—Virtual Pressroom.

Roesch, "Snort—Lightweight Intrusion Detection for Networks", Proceedings of LISA '99: 13th Systems Administration Conference; Nov. 7-12, 1999; pp. 229-238; USENIX Association, Seattle, WA USA.

Roy, "A bounded search algorithm for segmented channel routing for FPGA's and associated channel architecture issues", IEEE, Nov. 11, 1993, pp. 1695-1705, vol. 12.

Sachin Tandon, "A Programmable Architecture for Real-Time Derivative Trading", Master's Thesis, University of Edinburgh, 2003.

Schmerken, "With Hyperfeed Litigation Pending, Exegy Launches Low-Latency Ticker Plant", in Wall Street & Technology Blog, Mar. 20, 2007, pp. 1-2.

Schmit, "Incremental Reconfiguration for Pipelined Applications", FPGAs for Custom Computing Machines, Proceedings, The 5th Annual IEEE Symposium, Dept. of ECE, Carnegie Mellon University, Apr. 16-18, 1997, pp. 47-55, Pittsburgh, PA.

Schuehler et al., "Architecture for a Hardware Based, TCP/IP Content Scanning System", IEEE Micro, 24(1):62-69, Jan.-Feb. 2004, USA.

Schuehler et al., "TCP-Splitter: A TCP/IP Flow Monitor in Reconfigurable Hardware", Hot Interconnects 10 (Hotl-10), Stanford, CA, Aug. 21-23, 2002, pp. 127-131.

Search Results from IEEE Xplore for "Deterministic Finite Automaton current states", dated Dec. 28, 2010, 2 pages, citing Cole, "Real-Time Computation by n-Dimensional Iterative Arrays of Finite-State Machines", 1966; Kashyap, "Syntactic Decision Rules for Recognition of Spoken Words and Phrases Using a Stochastic Automaton", 1979; Rouvellou et al., "Inference of a Probabilistic Finite State Machine from its Output", 1995; and Yi et al., "A Method of Instance Learning based on Finite-State Automaton and its Application on TCM Medical Cases", 2010, et. al.

Seki et al., "High Speed Computation of Shogi With FPGA", Proceedings of 58th Convention Architecture, Software Science, Engineering, Mar. 9, 1999, pp. 1-133-1-134.

Shah, "Understanding Network Processors", Version 1.0, University of California—Berkeley, Sep. 4, 2001.

Shalunov et al., "Bulk TCP Use and Performance on Internet 2", ACM SIGCOMM Internet Measurement Workshop, 2001.

Shirazi et al., "Quantitative Analysis of Fpga-based Database Searching", Journal of VLSI Signal Processing Systems for Signal, Image, and Video Technology, May 2001, pp. 85-96, vol. 28, No. 1/2, Kluwer Academic Publishers, Dordrecht, NL.

Sidhu et al., "Fast Regular Expression Matching Using FPGAs", IEEE Symposium on Field Programmable Custom Computing Machines (FCCM 2001), Apr. 2001.

Sidhu et al., "String Matching on Multicontext FPGAs Using Self-Reconfiguration", FPGA '99: Proceedings of the 1999 ACM/SIGDA 7th International Symposium on Field Programmable Gate Arrays, Feb. 1999, pp. 217-226.

Singh et al., "The EarlyBird System for Real-Time Detection on Unknown Worms", Technical report CS2003-0761, Aug. 2003.

Sourdis and Pnevmatikatos, "Fast, Large-Scale String Match for a 10Gbps FPGA-based Network Intrusion Detection System", 13th International Conference on Field Programmable Logic and Applications, 2003.

Steinbach et al., "A Comparison of Document Clustering Techniques", KDD Workshop on Text Mining, 2000.

Tan et al., "A High Throughput String Matching Architecture for Intrusion Detection and Prevention", ISCA 2005: 32nd Annual International Symposium on Computer Architecture, pp. 112-122, 2005.

Tang et al., "A Novel Data Format Conversion Method Based on FPGA", Cross Strait Quad-Regional Radio Science and Wireless Technology Conference, Jul. 26, 2011, pp. 1204-1207.

Tau et al., "Transit Note #114: A First Generation DPGA Implementation", Jan. 1995, 9 pages.

Taylor et al., "Dynamic Hardware Plugins (DHP): Exploiting Reconfigurable Hardware for High-Performance Programmable Routers", Computer Networks, 38(3): 295-310 (16), Feb. 21, 2002, and online at http://www.cc.gatech.edu/classes/AY2007/cs8803hpc_fall/papers/phplugins.pdf.

Taylor et al., "Generalized RAD Module Interface Specification of the Field Programmable Port Extender (FPX) Version 2", Washington University, Department of Computer Science, Technical Report, Jul. 5, 2001, pp. 1-10.

(56) References Cited

OTHER PUBLICATIONS

Taylor et al., "Modular Design Techniques for the FPX", Field Programmable Port Extender: Jan. 2002 Gigabit Workshop Tutorial, Washington University, St. Louis, MO, Jan. 3-4, 2002.
Taylor et al., "Scalable Packet Classification using Distributed Crossproducting of Field Labels", Proceedings of IEEE Infocom, Mar. 2005, pp. 1-12, vol. 20, No. 1.
Taylor, "Models, Algorithms, and Architectures for Scalable Packet Classification", doctoral thesis, Department of Computer Science and Engineering, Washington University, St. Louis, MO, Aug. 2004, pp. 1-201.
Thomson Reuters, "Mellanox InfiniBand Accelerates the Exegy Ticker Plant at Major Exchanges", Jul. 22, 2008, URL: http://www.reuters.com/article/pressRelease/idUS125385+22-Jul-2008+BW20080722.
Uluski et al., "Characterizing Antivirus Workload Execution", SIGARCH Comput. Archit. News, vol. 33, No. 1, pp. 90-98, Mar. 2005.
Villasenor et al., "Configurable Computing Solutions for Automatic Target Recognition", FPGAS for Custom Computing Machines, 1996, Proceedings, IEEE Symposium on Napa Valley, CA, Apr. 17-19, 1996, pp. 70-79, 1996 IEEE, Napa Valley, CA, Los Alamitos, CA, USA.
Waldvogel et al., "Scalable High-Speed Prefix Matching", ACM Transactions on Computer Systems, Nov. 2001, pp. 440-482, vol. 19, No. 4.
Ward et al., "Dynamically Reconfigurable Computing: A Novel Computation Technology with Potential to Improve National Security Capabilities", May 15, 2003, A White Paper Prepared by Star Bridge Systems, Inc. [retrieved Dec. 12, 2006]. Retrieved from the Internet: <URL: http://www.starbridgesystems.com/resources/whitepapers/Dynamically%20Reconfigurable%20Computing.pdf.
Weaver et al., "Very Fast Containment of Scanning Worms", Proc. USENIX Security Symposium 2004, San Diego, CA, Aug. 2004, located at http://www.icsi.berkely.edu/~nweaver/containment/containment.pdf.
Web-Pop (Professional Options Package) (www.pmpublishing.com).
West et al., "An FPGA-Based Search Engine for Unstructured Database", Proc. of 2nd Workshop on Application Specific Processors, Dec. 2003, San Diego, CA.
Wooster et al., "HTTPDUMP Network HTTP Packet Snooper", Apr. 25, 1996.
Yamaguchi et al., "An Approach for Homology Search with Reconfigurable Hardware", Google, 2001, pp. 374-375.
Yamaguchi et al., "High Speed Homology Search with FPGAs", Proceedings Pacific Symposium on Biocomputing, Jan. 3-7, 2002, pp. 271-282, vol. 7, Online, Lihue, Hawaii, USA.
Yan et al., "Enhancing Collaborative Spam Detection with Bloom Filters", 2006, IEEE, pp. 414-425.
Yoshitani et al., "Performance Evaluation of Parallel Volume Rendering Machine Re Volver/C40", Study Report of Information Processing Society, Mar. 5, 1999, pp. 79-84, vol. 99, No. 21.
Office Action for EP Application 13849798.7 dated Apr. 17, 2019.

\* cited by examiner

METHOD AND APPARATUS FOR ACCELERATED FORMAT TRANSLATION OF DATA IN A DELIMITED DATA FORMAT

CROSS-REFERENCE AND PRIORITY CLAIM TO RELATED PATENT APPLICATIONS

This patent application is a continuation of U.S. patent application Ser. No. 14/060,313, filed Oct. 22, 2013, and entitled "Method and Apparatus for Accelerated Format Translation of Data in a Delimited Data Format", now U.S. Pat. No. 9,633,093, which claims priority to U.S. provisional patent application Ser. No. 61/717,496, filed Oct. 23, 2012, and entitled "Method and Apparatus for Accelerated Format Translation of Data in a Delimited Data Format", the entire disclosures of each of which are incorporated herein by reference.

INTRODUCTION

A delimited data format is a common format used for passing data between data processing systems or over networks, particularly with respect to passing record-oriented data. Delimited data formats are platform-independent, and they use a very simple set of tags to represent data. With a delimited data format, data characters are organized into a plurality of fields. A field delimiter (FDL) character is used to separate data fields, a record delimiter (RDL) character is used to separate records, and a shield character is used to shield data characters within data fields that also happen to serve as the field delimiter character or the record delimiter character.

The comma separated value (CSV) format is a common delimited data format. With the CSV format, a comma is typically used as the FDL character, a newline is typically used as the RDL character, and a quotation mark is typically used as the shield character. However, other characters can be employed. For example, a pipe or tab character as the FDL character, an apostrophe character as the shield character, etc. FIG. 1 shows an exemplary portion of a record in a delimited data format.

In the example of FIG. 1, the record is a patient medical record 100 comprising a plurality of different fields (e.g., name, address, etc.). The data from this record 100 can be represented in the CSV format via data 102 in FIG. 1. Each field 104$i$ of the record can be separated by the FDL character 106. However, it may be the case that the character used as the FDL character 106 also exists within the data as a data character. In the example of FIG. 1, this is shown by the commas 110 that are present in the data for Fields 1 and 3 ($104_1$ and $104_3$). In such situations, to prevent a misinterpretation of these commas as field delimiters, the CSV format operates to use a shield character 108 at the start and end of the field that contains the data character 110 which matches the FDL character 106. In the example of FIG. 1, quote marks serve as the shield character 108. Thus, the data St. Louis, Mo. becomes "St. Louis, Mo.". The use of shield characters raises another possible misinterpretation with respect to data characters 112 in a field that happen to match the shield character 108 (see the quotation marks used for the data string ("Jim") in Field 1 ($100_1$)). To prevent a misinterpretation of these quotation marks as shield characters, the CSV format also operates to use a shield character 108 adjacent the data character that happens to match the shield character. Thus, the data string ("Jim") appears as (""Jim"") in the CSV format.

Delimited data formats present significant challenges in connection with processing the delimited data using software. The inherently serial process of moving byte by byte through a file to look for delimiters and shield characters does not map well to general purpose processors. For example, suppose it is desired to validate whether the zip code field of the file shown in FIG. 1 contains a valid zip code. A software-based system would need to process each byte of the file up through Field 4 ($104_4$) in order to know that Field 4 has been located. Only then can the processing software validate the zip code data. This byte-by-byte processing requirement creates a bottleneck that detracts from the throughput of a processing system.

As solution to this problem, the inventors disclose various techniques for performing high speed format translations of incoming data, where the incoming data is arranged in a delimited data format.

In accordance with an exemplary aspect disclosed herein, the data in the delimited data format can be translated into outgoing data having a structured format, the structured format being configured to permit a downstream processing component to jump directly to a field of interest in the outgoing data without requiring that component to analyze all of the bytes leading up to the field of interest.

An example of a structured format that can be used toward this end is a fixed field format. With a fixed field format, each field of the outgoing data has a fixed length and is populated with data characters that belong to the same field of the incoming data. If there are not enough data characters for that incoming field to fill the fixed length of the outgoing field, then padding characters can be added to the outgoing field. By employing fields of a fixed length, any downstream processing can quickly and easily target specific fields of the outgoing data for further processing by simply jumping to the location of the targeted field. Because the fixed field layout is well-defined, a downstream processing component will be able to know the byte offset for the field of interest, which means that only simple pointer arithmetic would be needed for the processing component to jump to the field of interest.

In an exemplary embodiment, a reconfigurable logic device can be employed to perform this data translation. As used herein, the term "reconfigurable logic" refers to any logic technology whose form and function can be significantly altered (i.e., reconfigured) in the field post-manufacture. This is to be contrasted with a general purpose processor (GPP), whose function can change post-manufacture, but whose form is fixed at manufacture. An example of a reconfigurable logic device is a programmable logic device (PLD), such as a field programmable gate array (FPGA). As used herein, the term "general-purpose processor" (or "GPP") refers to a hardware device having a fixed form and whose functionality is variable, wherein this variable functionality is defined by fetching instructions and executing those instructions, of which a conventional central processing unit (CPU) is a common example. Exemplary embodiments of GPPs include an Intel Xeon processor and an AMD Opteron processor. Furthermore, as used herein, the term "software" refers to data processing functionality that is deployed on a GPP or other processing devices, wherein software cannot be used to change or define the form of the device on which it is loaded. By contrast, the term "firmware", as used herein, refers to data processing functionality that is deployed on reconfigurable logic or other processing devices, wherein firmware may be used to change or define the form of the device on which it is loaded.

Furthermore, the data translation task can be broken down into a plurality of subtasks, where each subtask can be performed by a plurality of data processing modules arranged to operate in a pipelined fashion with respect to each other. Thus, while a downstream module in the pipeline is performing a subtask on data that was previously processed by an upstream module in the pipeline, the upstream module in the pipeline can be simultaneously performing its subtask on more recently received data. An exemplary data translation pipeline can comprise (1) a first module configured to convert the incoming data arranged in the delimited data format to an internal format stripped of the field delimiter characters and the record delimiter characters of the incoming data while preserving the data characters of the incoming fields, (2) a second module downstream from the first module, the second module configured to remove the shield characters from the converted data having the internal format, and (3) a third module downstream from the second module, the third module configured to translate the output of the second module to the outgoing data having the fixed field format.

Through such a modular approach, the pipeline is amenable to accelerated data translation via any of a number of platforms. As mentioned above, reconfigurable logic can be used as a platform for deploying the modules as hardware logic operating at hardware processing speeds via firmware deployed on a reconfigurable logic device. Moreover, such a pipeline is also amenable to implementation on graphics processor units (GPUs), application-specific integrated circuits (ASICs), chip multi-processors (CMPs), and other multi-processor architectures.

The inventors also disclose that the pipeline can be configured to ingest and process multiple characters per clock cycle. This data parallelism can be another source for acceleration relative to conventional solutions.

These and other features and advantages of the present invention will be described hereinafter to those having ordinary skill in the art.

DETAILED DESCRIPTION

Figure 1:
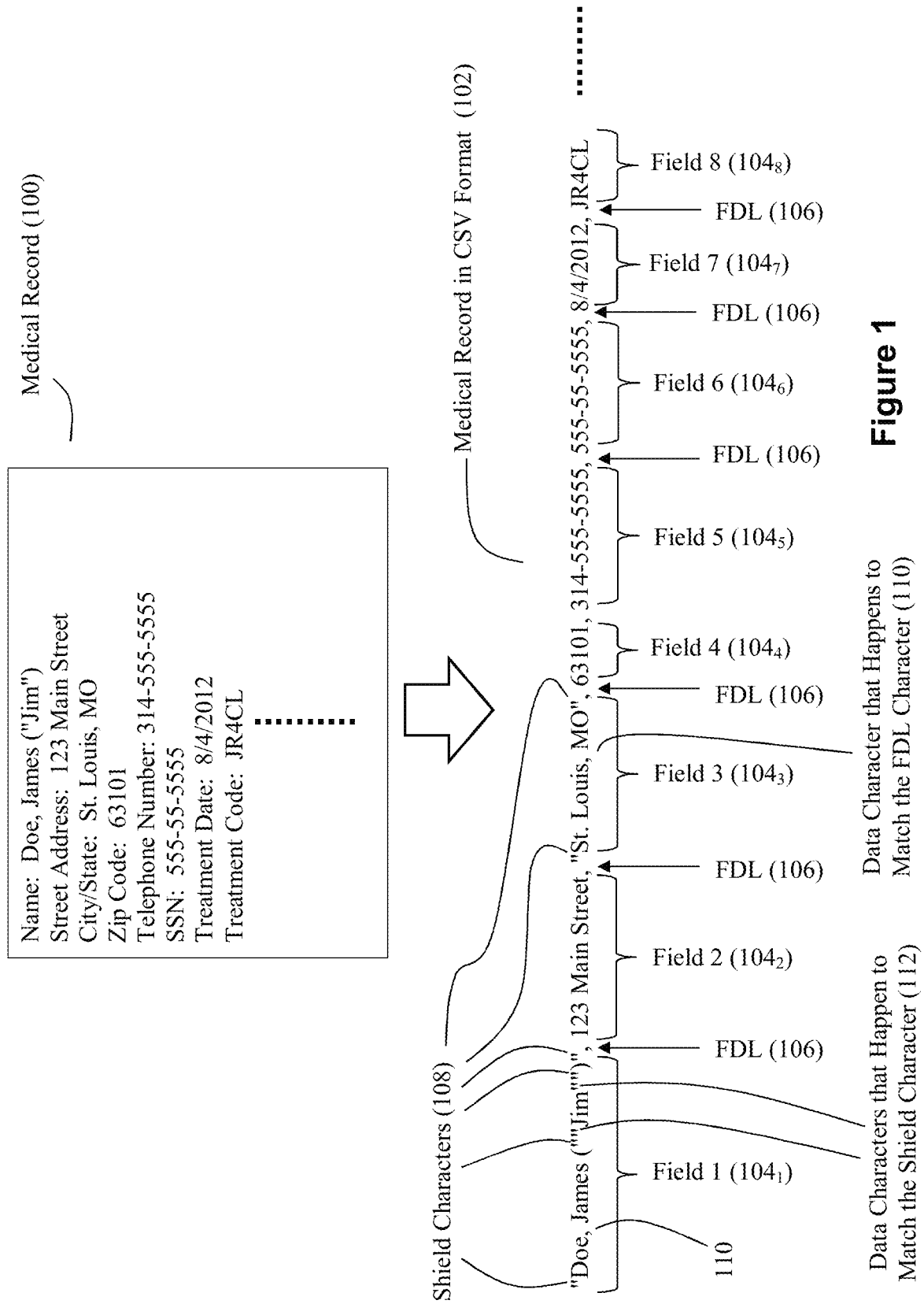
FIG. 1 depicts an example of data organized into a delimited data format.
Figure 2:
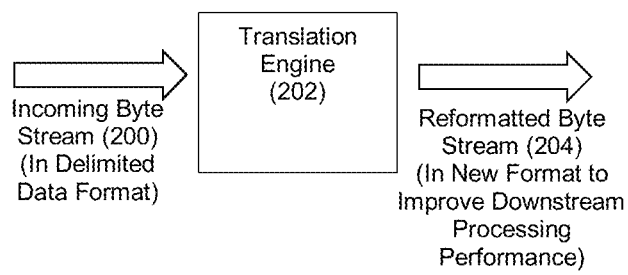
FIG. 2 depicts an exemplary translation engine in accordance with a disclosed embodiment.

FIG. 2 depicts an exemplary translation engine 202 that is configured to translate an incoming byte stream 200 having a delimited data format into a reformatted byte stream 204 having the structured format that is geared toward high performance downstream processing such that a downstream processing component can jump directly to fields without analyzing the data characters of the reformatted byte stream 204. As noted, this structured format can be a fixed field format. Once again, FIG. 1 shows exemplary data that can serve as byte stream 200. As will be understood, the bytes of the byte stream 200 can serve as data characters, record delimiters characters, field delimiter characters, and shield characters.

Figure 3:
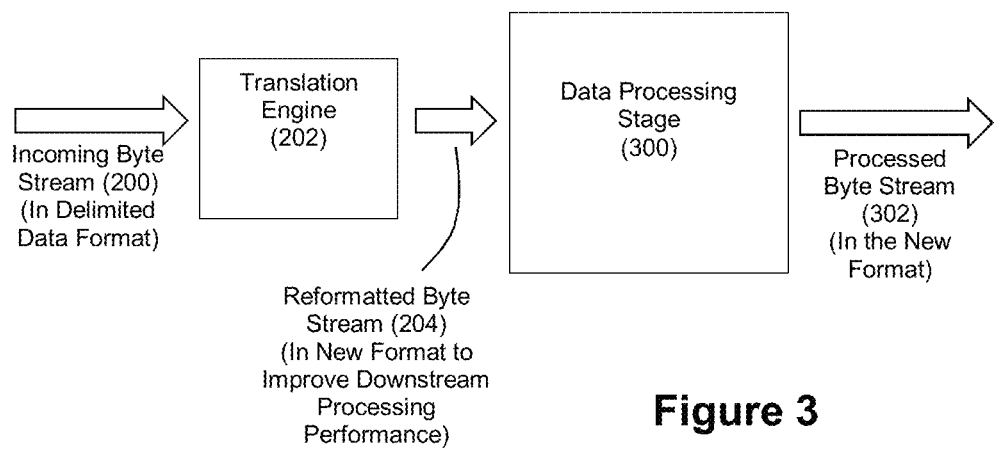
FIG. 3 depicts an exemplary system comprising a translation engine and a data processing stage downstream from the translation engine.

FIG. 3 shows the delivery of the reformatted byte stream 204 to a data processing stage. The data processing stage will be able to select fields of the reformatted byte stream for targeted processing without further analyzing the data characters of the reformatted byte stream 204, thereby greatly improving the throughput performance of the system. The data processing stage then performs data processing operations on the selected fields to generate a processed byte stream 302. This processed byte stream 302 can also exhibit the structured format of the reformatted byte stream 204. The data processing stage 300 can be implemented in software via a GPP, in firmware via reconfigurable logic, or any other platform desired by a practitioner.

For example, the data processing stage can be configured to perform various processing operations as part of data quality checking in connection with extract, transfer, and load (ETL) operations for a database. Some exemplary processing operations can include:

Address Validation: A field expected to contain an address can have the address data validated as to whether it exhibits a correct postal service-recognized address format.

Email Validation: A field expected to contain an email address can be validated as to whether it exhibits a correct email address format.

Date Validation: A field expected to contain a date can be validated as to whether it exhibits a date in the correct range and format.

Query/Replace: The data characters in a selected field can be translated from one set to another set (e.g., mapping codes from one code set to another code set or replacing codes with natural language descriptions of such codes).

Field Masking/Tokenization: The data characters in a select field can be obfuscated or tokenized for security purposes.

Filtering/Searching: The data characters in selected fields can be matched against various search criteria.

It should be understood that these are but a few of exemplary data processing operations that can be performed by the data processing stage 300.

Furthermore, it should be understood that these data processing operations can be legacy data processing operations that are implemented in software on processors of a practitioner. Also, if desired, a practitioner can deploy such data processing operations via reconfigurable logic to achieve still further acceleration. Examples of hardware-accelerated data processing operations that can be performed by the data processing stage 300 include the data processing operations disclosed by U.S. Pat. Nos. 7,636,703, 7,702,629, 8,095,508 and U.S. Pat. App. Pubs. 2007/0237327, 2008/0114725, 2009/0060197, and 2009/0287628, the entire disclosures of each of which being incorporated herein by reference.

Figure 4:
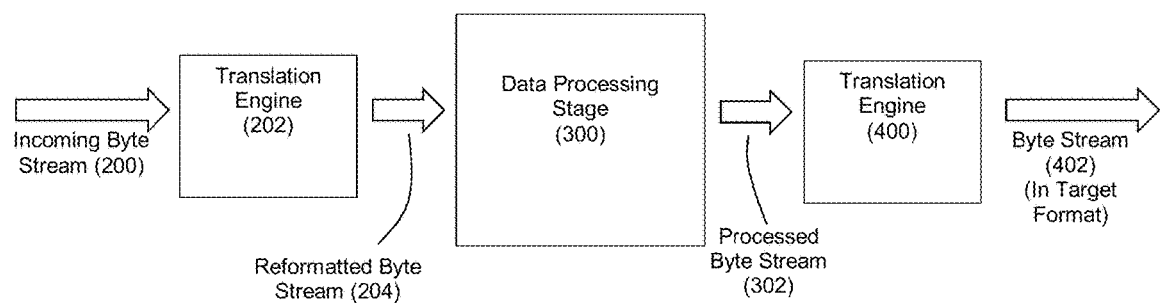
FIG. 4 depicts an exemplary system comprising a translation engine, a data processing stage downstream from the translation engine, and a translation engine downstream from the data processing stage.

FIG. 4 depicts an exemplary embodiment where the processed byte stream 302 is translated by a translation engine 400 into a byte stream 402 having a target format. For example, a practitioner may desire that the system re-translate the byte stream 302 back into a delimited data format. In such an embodiment, the translation engine 400 can perform the complementary inverse of the translation operations performed by translation engine 202 to return the data to the delimited data format. Translation engine 400 can also be hardware-accelerated via reconfigurable logic and modularized via processing modules arranged in a pipeline as explained in connection with the translation engine 202.

Figure 5:
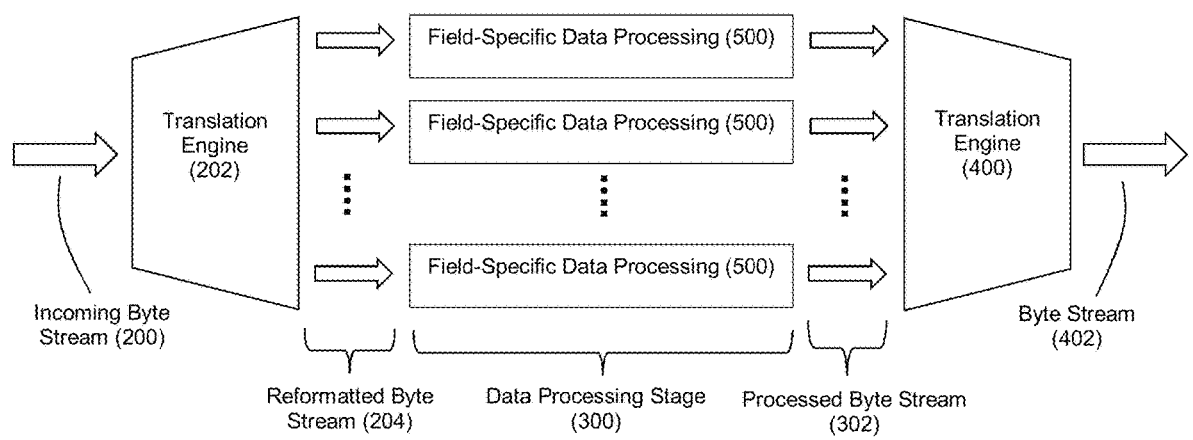
FIG. 5 depicts an exemplary system similar to that of FIG. 4, specifically showing field-specific data processing operations within the data processing stage.

FIG. 5 depicts a similar system that highlights how the output of the translation engine 202 can feed field-specific data processing operations 500 at the data processing stage 300. It should also be understood that for software-based embodiments of the data processing stage 300, record-specific threads can be running in parallel to provide additional acceleration.

Figure 6:
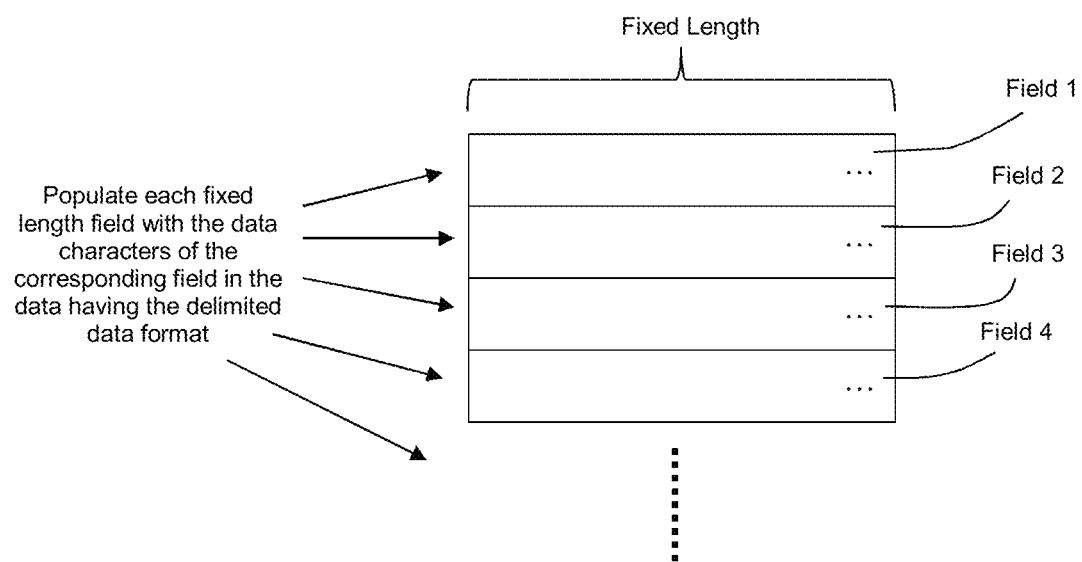
FIG. 6 depicts an exemplary fixed field format.
Figure 7:
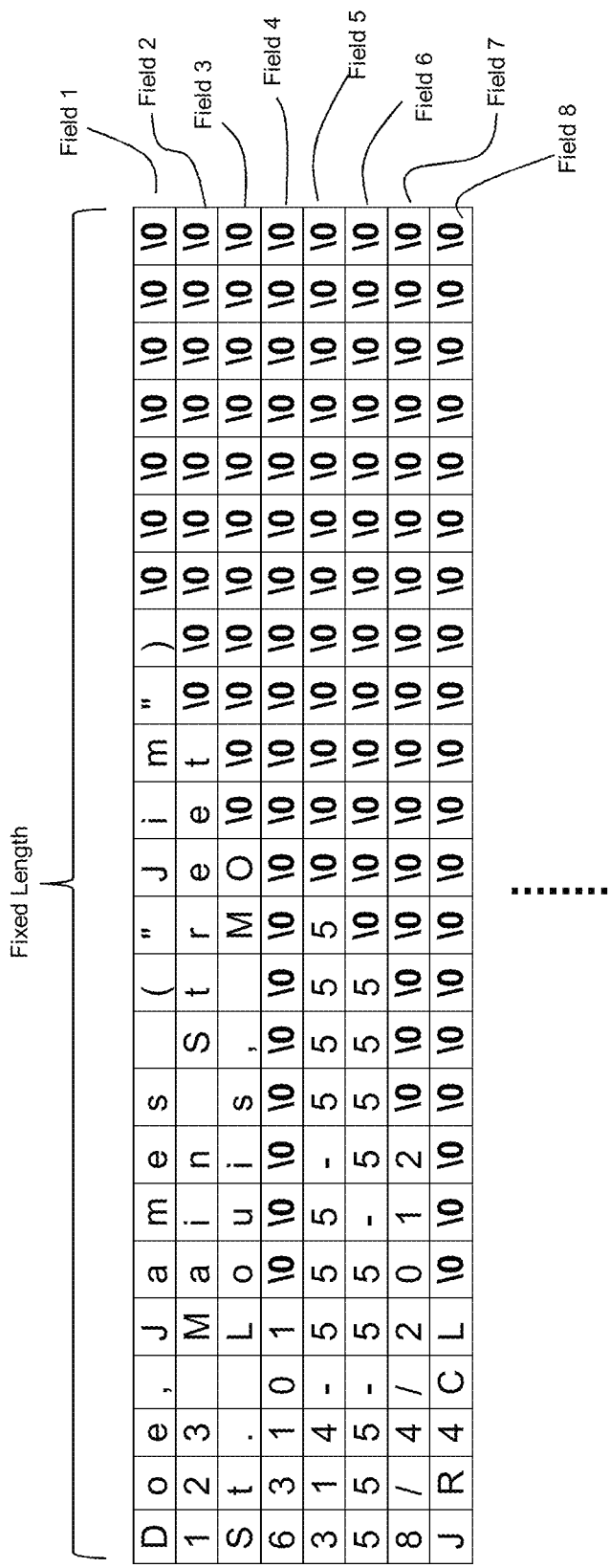
FIG. 7 depicts the data of FIG. 1 organized in a fixed field format.

FIG. 6 depicts an exemplary fixed field format that can be exhibited by byte stream 204. Each field of the data has a fixed length (e.g, 128 bytes, etc.). The translation engine 202 can operate to populate each field of the fixed field output with data characters of the corresponding field in the byte stream having the delimited data format. Should there not be enough data characters in the byte stream to fill the fixed field, padding characters can be added to complete the field. In the event that there is insufficient space in the fixed field for all data characters in a field of the delimited data format byte stream, the translation engine 202 can flag a data overflow condition and take appropriate measures through exception handling logic. FIG. 7 depicts an example where the data of FIG. 1 has been translated into a fixed field format where each field has a fixed length of 24 bytes. It should be well understood that a field length of 24 bytes is exemplary only, and other field lengths can be readily employed. It should also be understood that each field need not have the same fixed length. For example, a practitioner can choose to define a field length of 36 bytes for Field 1, a field length of 64 bytes for Field 2, a field length of 64 bytes for Field 3, a field length of 16 bytes for Field 4, and so on. A practitioner can choose such fixed field lengths for each field based on expected characteristics of the data.

In an embodiment where the translation engine 202 is implemented in reconfigurable logic, examples of suitable platforms for such a translation engine 202 are shown in FIGS. 8(*a*) and (b). FIG. 8(*a*) depicts a system 800 employs a hardware-accelerated data processing capability through coprocessor 840 to process the incoming byte stream 200. Within system 800, a coprocessor 840 is positioned to receive byte stream 200 that streams into the system 800 from a network 820 (via network interface 810).

The computer system defined by processor 812 and RAM 808 can be any commodity computer system as would be understood by those having ordinary skill in the art. For example, the computer system may be an Intel Xeon system or an AMD Opteron system. Thus, processor 812, which serves as the central or main processor for system 800, preferably comprises a GPP (although this need not be the case).

In this exemplary embodiment, the coprocessor 840 comprises a reconfigurable logic device 802. Preferably, the byte stream 200 streams into the reconfigurable logic device 802 by way of system bus 806, although other design architectures are possible (see FIG. 9(*b*)). The reconfigurable logic device 802 can be a field programmable gate array (FPGA), although this need not be the case. System bus 806 can also interconnect the reconfigurable logic device 802 with the processor 812 as well as RAM 808. In an exemplary embodiment, system bus 806 may be a PCI-X bus or a PCI-Express bus, although this need not be the case.

The reconfigurable logic device 802 has firmware modules deployed thereon that define its functionality. The firmware socket module 804 handles the data movement requirements (both command data and target data) into and out of the reconfigurable logic device, thereby providing a consistent application interface to the firmware application module (FAM) chain 850 that is also deployed on the reconfigurable logic device. The FAMs 850i of the FAM chain 850 are configured to perform specified data processing operations on any data that streams through the chain 850 from the firmware socket module 804. Examples of FAMs that can be deployed on reconfigurable logic in accordance with the exemplary translation engine 202 are described below.

The specific data processing operation that is performed by a FAM is controlled/parameterized by the command data that FAM receives from the firmware socket module 804. This command data can be FAM-specific, and upon receipt of the command, the FAM will arrange itself to carry out the data processing operation controlled by the received command. For example, within a FAM that is configured to perform a shield character find operation, the FAM's shield character find operation can be parameterized to define the character that will be used as the shield character. In this way, a FAM that is configured to perform a shield character find operation can be readily re-arranged to perform a different shield character find operation by simply loading parameters for a new shield character in that FAM. As another example, a command can be issued to the one or more FAMs that are configured to find a delimiter character (e.g., a record delimiter character or field delimiter character)

so that the FAM can be tailored to different delimiter characters without requiring a full reconfiguration of the reconfigurable logic device.

Once a FAM has been arranged to perform the data processing operation specified by a received command, that FAM is ready to carry out its specified data processing operation on the data stream that it receives from the firmware socket module. Thus, a FAM can be arranged through an appropriate command to process a specified stream of data in a specified manner. Once the FAM has completed its data processing operation, another command can be sent to that FAM that will cause the FAM to re-arrange itself to alter the nature of the data processing operation performed thereby. Not only will the FAM operate at hardware speeds (thereby providing a high throughput of data through the FAM), but the FAMs can also be flexibly reprogrammed to change the parameters of their data processing operations.

The FAM chain 850 preferably comprises a plurality of firmware application modules (FAMs) 850a, 850b, . . . that are arranged in a pipelined sequence. However, it should be noted that within the firmware pipeline, one or more parallel paths of FAMs 850i can be employed. For example, the firmware chain may comprise three FAMs arranged in a first pipelined path (e.g., FAMs 850a, 850b, 850c) and four FAMs arranged in a second pipelined path (e.g., FAMs 850d, 850e, 850f, and 850g), wherein the first and second pipelined paths are parallel with each other. Furthermore, the firmware pipeline can have one or more paths branch off from an existing pipeline path. A practitioner of the present invention can design an appropriate arrangement of FAMs for FAM chain 850 based on the processing needs of a given translation operation.

A communication path 830 connects the firmware socket module 804 with the input of the first one of the pipelined FAMs 850a. The input of the first FAM 850a serves as the entry point into the FAM chain 850. A communication path 832 connects the output of the final one of the pipelined FAMs 850m with the firmware socket module 804. The output of the final FAM 850m serves as the exit point from the FAM chain 850. Both communication path 830 and communication path 832 are preferably multi-bit paths.

The nature of the software and hardware/software interfaces used by system 800, particularly in connection with data flow into and out of the firmware socket module are described in greater detail in U.S. Patent Application Publication 2007/0174841, the entire disclosure of which is incorporated herein by reference.

Figure 8A:
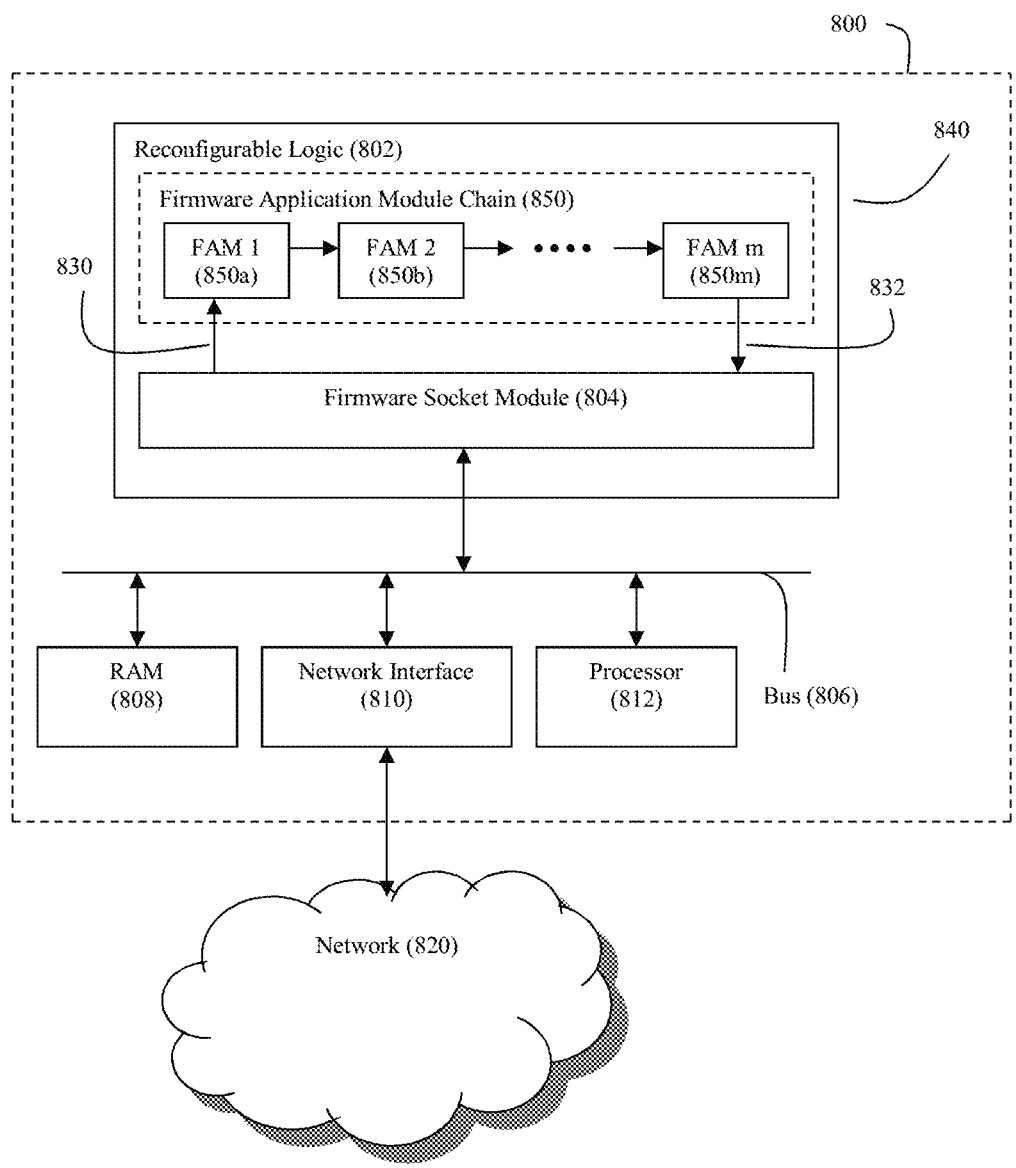
FIGS. 8(a) and (b) depict examples of suitable platforms for the translation engine.
Figure 8B:
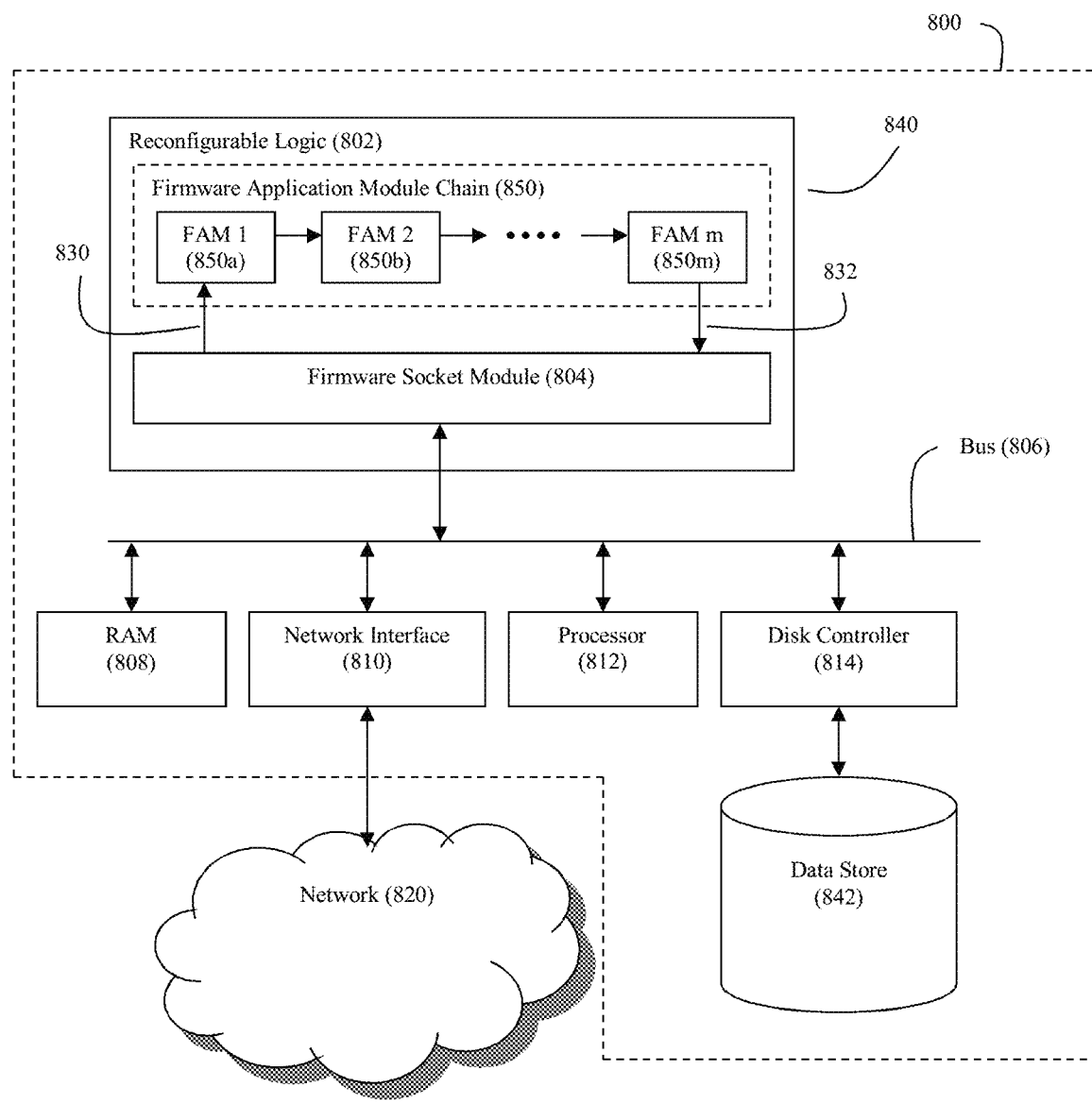

FIG. 8(b) depicts another exemplary embodiment for system 800. In the example of FIG. 8(b), system 800 includes a data store 842 that is in communication with bus 806 via disk controller 814. Thus, the byte stream 200 that is streamed through the coprocessor 840 may also emanate from data store 842. Furthermore, the data store 842 can be the target destination for the output from the translation engine 202 and/or the data processing stage 300 if desired by a practitioner. Data store 842 can be any data storage device/system, but it is preferably some form of mass storage medium. For example, data store 842 can be a magnetic storage device such as an array of Seagate disks.

Figure 9A:
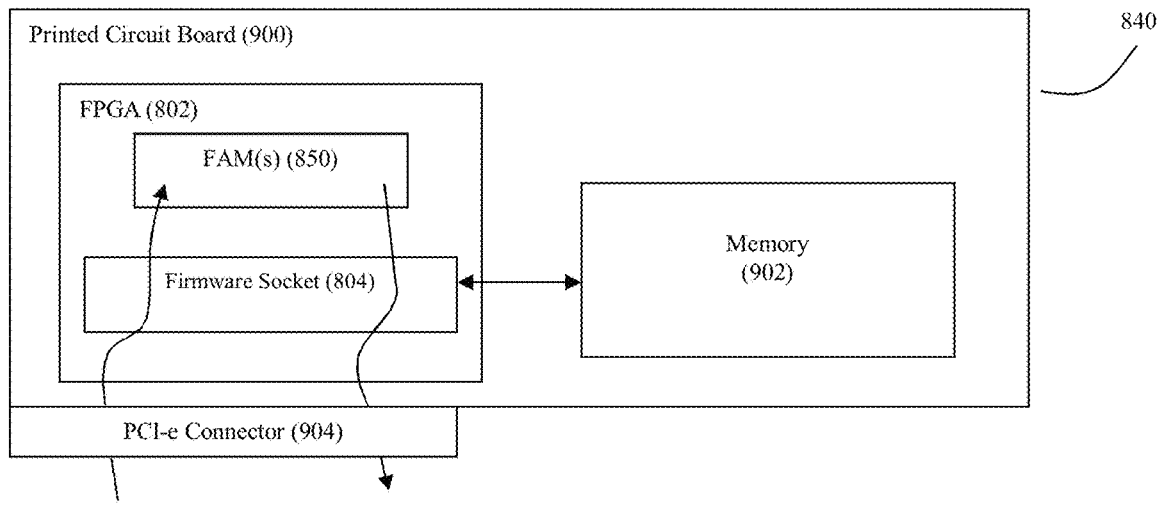
FIGS. 9(a) and (b) depict exemplary printed circuit boards for use as a coprocessor for the embodiments of FIGS. 8(a) and (b).

FIG. 9(a) depicts a printed circuit board or card 900 that can be connected to the PCI-X or PCI-e bus 806 of a commodity computer system for use as a coprocessor 840 in system 800 for any of the embodiments of FIGS. 8(a)-(b). In the example of FIG. 9(a), the printed circuit board includes an FPGA 802 (such as a Xilinx Virtex 5 or an Altera Stratix V FPGA) that is in communication with a memory device 902 and a PCI-e bus connector 904. A preferred memory device 902 comprises SRAM and DRAM memory. A preferred PCI-X or PCI-e bus connector 904 is a standard card edge connector.

Figure 9B:
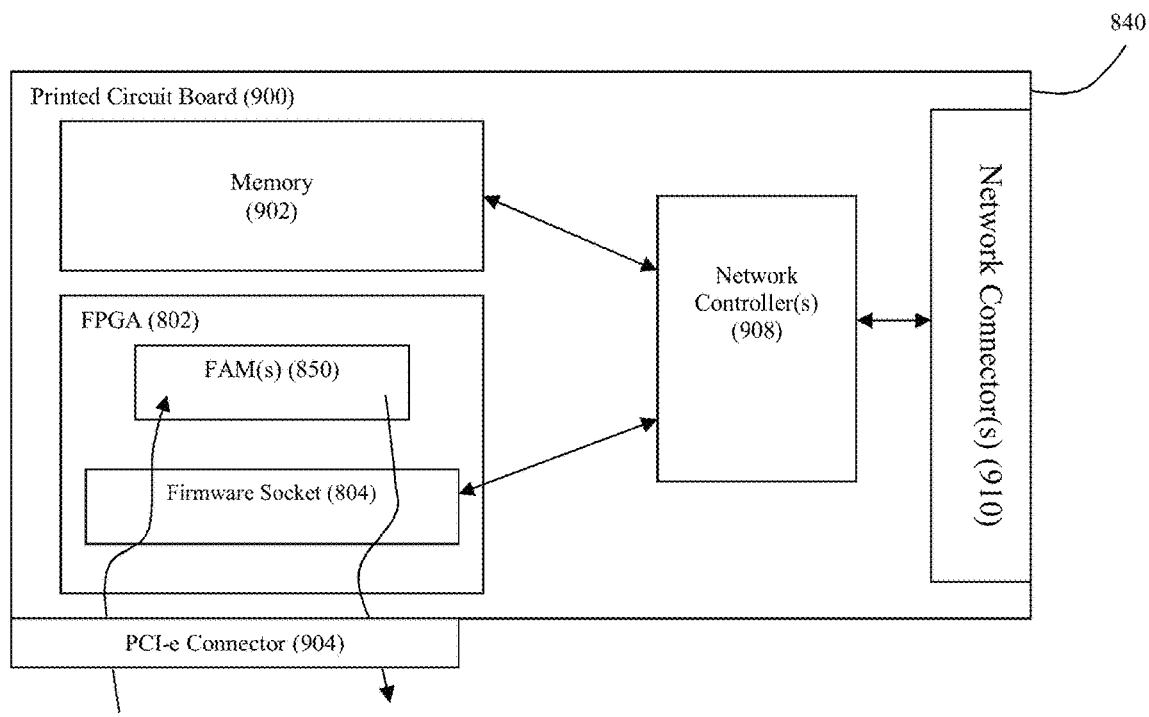

FIG. 9(b) depicts an alternate configuration for a printed circuit board/card 900. In the example of FIG. 9(b), one or more network controllers 908, and one or more network connectors 910 are also installed on the printed circuit board 900. Any network interface technology can be supported, as is understood in the art. Hardware logic can be used as the internal connector between the FPGA, memory, and network controller. It should be noted that a disk interface technology can be used in addition to or in place of the network controller and network connector shown in FIG. 9(b).

Figure 10:
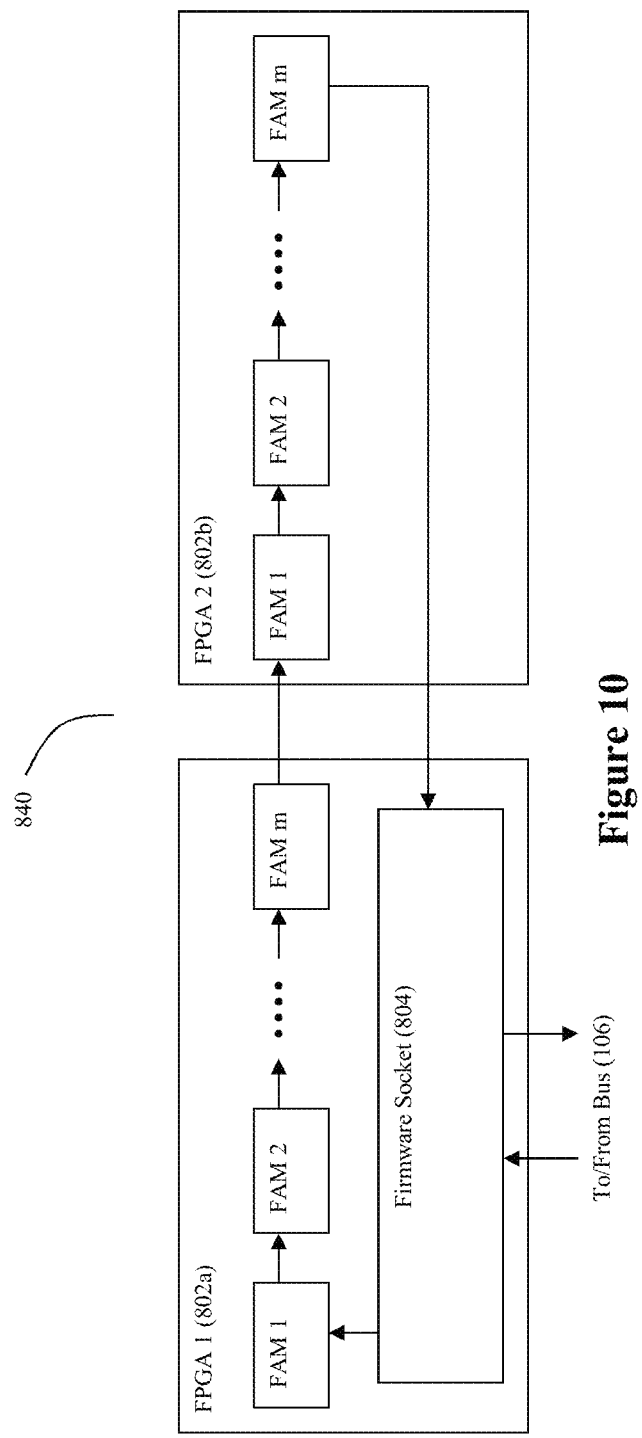
FIG. 10 depicts an example of how a firmware pipeline can be deployed across multiple reconfigurable logic devices.

It is worth noting that in either the configuration of FIG. 9(a) or 9(b), the firmware socket 804 can make memory 902 accessible to the bus 806, which thereby makes memory 902 available for use by an OS kernel as the buffers for transfers to the FAMs from a data source with access to the bus. It is also worth noting that while a single FPGA 802 is shown on the printed circuit boards of FIGS. 9(a) and (b), it should be understood that multiple FPGAs can be supported by either including more than one FPGA on the printed circuit board 900 or by installing more than one printed circuit board 900 in the system 800. FIG. 10 depicts an example where numerous FAMs in a single pipeline are deployed across multiple FPGAs.

Translation Engine 202

Figure 11:
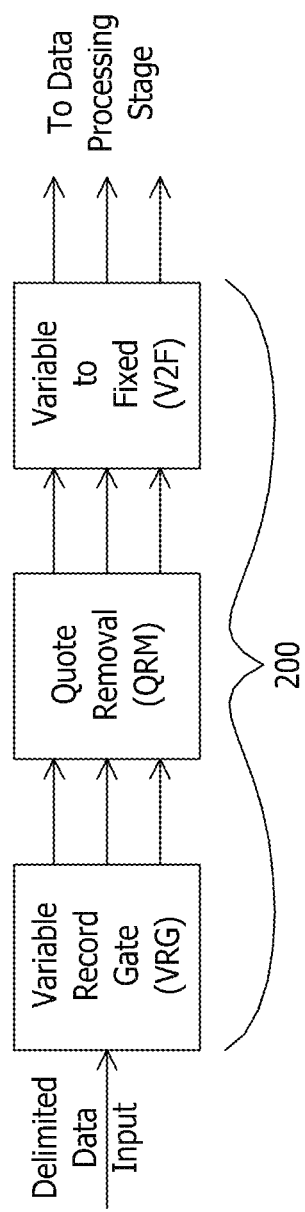
FIG. 11 depicts an example of a pipeline that can be deployed by a translation engine to convert delimited data to fixed field data.

FIG. 11 depicts an exemplary pipeline that can be employed by the translation engine 202. The pipeline can comprise (1) a first module configured to convert the incoming data arranged in the delimited data format to an internal format stripped of the field delimiter characters and the record delimiter characters of the incoming data while preserving the data characters of the incoming fields, (2) a second module downstream from the first module, the second module configured to remove the shield characters from the converted data having the internal format, and (3) a third module downstream from the second module, the third module configured to translate the output of the second module to the outgoing data having the fixed field format. In this example, the first module can be referred to as a variable record gate (VRG) module, the second module can be referred to as a quote removal module (QRM) given that quote marks are used as the shield character in this example, and the third module can be referred to as a variable-to-fixed (V2F) module. Each module can be configured to operate in parallel in a pipelined manner. As such, while the V2F module is operating on data previously processed by the VRG and QRM modules, the QRM module is operating on data previously processed by the VRG module, and the VRG module is operating on newly received data, and so on as data continues to stream into the pipeline.

Figure 12:
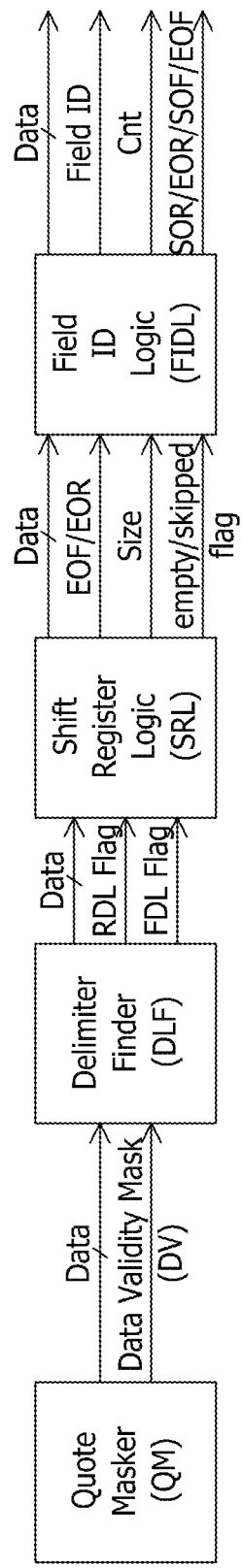
FIG. 12 depicts an exemplary pipeline for a variable record gate (VRG) module.

VRG Module:

FIG. 12 depicts an exemplary arrangement for a VRG module. The components of the VRG module shown in FIG. 12 can also be implemented as modular circuits in a pipelined chain. The VRG module can generate an output byte stream that is marked with control data to identify information such as which bytes correspond to a start of record, an end of record, a start of field, and an end of field. Thus, downstream modules need not reparse the bytes to gather that information. With reference to the operations described herein, it should be understood that the various circuit components of the VRG module can process the bytes of the byte stream in chunks (e.g., 64 bit (8 byte) or 128 bit (16 byte) chunks) per clock cycle. Thus, the component circuits can be configured to provide data parallelism by ingesting and processing multiple characters in the byte stream per clock cycle.

A first circuit in the VRG can be configured to process the shield characters that are present in the byte stream 200 to distinguish between the bytes that are eligible for downstream consideration as to whether they correspond to a delimiter character (e.g., the bytes that are present in a field that has not been shielded by a shield character) and the bytes that are ineligible for downstream consideration as to whether they correspond to a delimiter character (e.g., the bytes that are present in a field that has been shielded by a shield character). In this example, such a circuit can be referred to as a quote masker (QM) circuit.

A second circuit in the VRG that is downstream from the QM circuit can be configured to process the output of the QM circuit to locate the presence of delimiter characters in the byte stream. In this example, such a circuit can be referred to as a delimiter finder (DLF) circuit.

A third circuit in the VRG that is downstream from the DLF circuit can be configured to process the output of the DLF circuit to detect empty fields, remove the delimiter characters from the byte stream, and mark the bytes which correspond to data characters at the start of a record and end of a record. In this example, such a circuit can be referred to as a shift register logic (SRL) circuit.

A fourth circuit in the VRG that is downstream from the SRL circuit can be configured to process the output of the SRL circuit to generate a field identifier that identifies which field each data character of the byte stream belongs to and mark the bytes which correspond to data characters at the start of a field and end of a field. In this example, such a circuit can be referred to as a field ID logic (FIDL) circuit.

Figure 13:
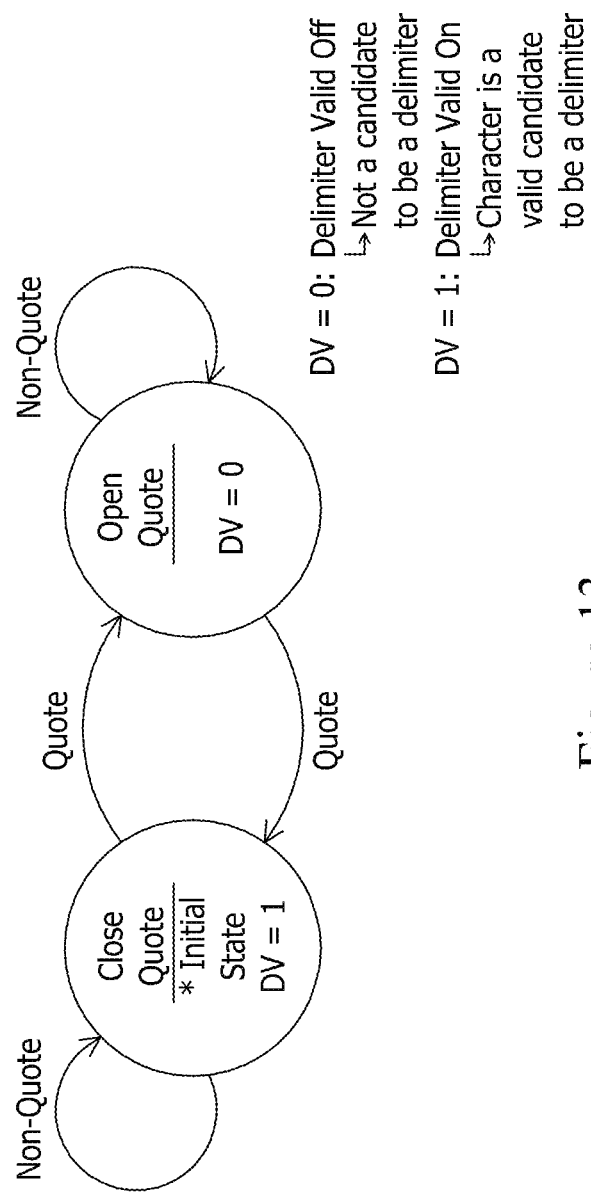
FIG. 13 depicts a state machine for an exemplary quote masker circuit.

FIG. 13 provides additional detail regarding the QM circuit. Once again, in this example, the shield character is a quote mark, so quotes will be used throughout this example to refer to the shield character. However, it should be understood that characters other than quote marks could be used as the shield character. As noted, the QM circuit is configured to mark each byte of the byte stream with an indicator of whether or not it is a valid candidate as a delimiter (i.e. NOT protected by the shield character). FIG. 13 depicts exemplary state diagrams that can be employed by the QM circuit to implement this task. FIG. 13 shows two states: CLOSED ("Close Quote") and OPEN ("Open Quote"). In the CLOSED state, which is the initialization state, the quotes have been closed, and characters are open for consideration as a delimiter. While in this state, any character that is not a quote character will be marked with a "Delimiter Valid" (DV) flag set to true, meaning that the character is a candidate delimiter character. Upon observing a quote character, this machine will transition to the OPEN state, meaning that the data is inside a quote and thus shielded by the quote character. Any character other than a quote character will be marked with a DV flag set to false, indicating that the character is not a candidate to be a delimiter. Upon detection of another quote character, this state machine will transition back to CLOSED, meaning that next character is no longer being shielded by quote marks. This toggling behavior also accommodates the possible presence of double quotes in the byte stream which are meant to internally shield data characters that happen to be quote marks (see the portion of Field 1 in FIG. 1 comprising "Jim"—all of Field 1 has been shielded by quote marks, so that quote mask should not change upon encountering the internal double quotes in the byte stream). From the open data state, if a quote mark is detected in the byte stream, the state machine will transition to the closed quote state, while any other character in the byte stream means the state machine will remain in the open data state.

It should be understood with the diagram of FIG. 13 that one can ignore the DV status bits for the actual quote characters because configuration restrictions prevent shield characters and delimiter characters from overlapping. In this model, some quotes will be marked as valid, and others will not, but regardless of their marking they will never be considered a delimiter, as will be understood upon review of FIG. 14.

The QM circuit thus outputs the bytes of the byte stream where each byte is associated with a DV flag to indicate whether the associated byte should be processed to assess whether it contains a delimiter character.

Figure 14A:
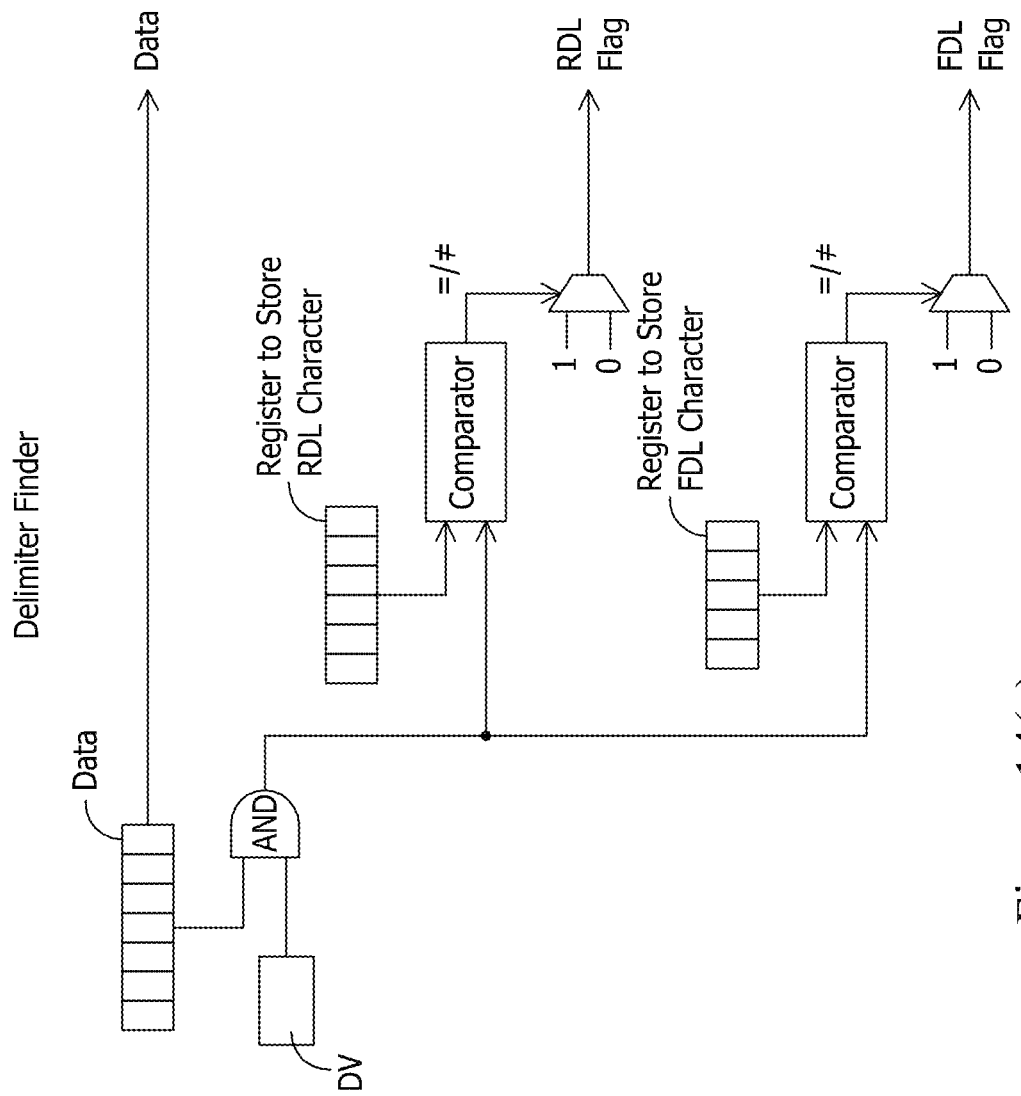
FIGS. 14(a) and (b) depict exemplary delimiter finder circuits.

FIG. 14(a) provides additional detail regarding an example of a DLF circuit. A data register can be loaded with the current byte under consideration. A mask register can be loaded with the DV flag associated with the byte loaded in the register. A first match key register can be loaded with the RDL character, and a second match key register can be loaded with the FDL character. The byte in the data register can be logically ANDed with the DV data in the mask register. Thus, from the description above, (1) if a byte has been identified by the QM register as being eligible for consideration as to whether it contains a delimiter character, its associated DV flag is equal to 1, and the output of the AND operation will pass the byte to a matching stage, and (2) if a byte has been identified by the DV register as being ineligible for consideration as to whether it contains a delimiter character, its associated DV flag is equal to 0, and the output of the AND operation will pass a zero value to a matching stage (thereby causing the matching stage to find no match with respect to the delimiter characters which are assumed to be different characters than the zero value).

A first comparator in the matching stage compares the RDL character with the AND operation output. Based on the outcome of that comparison, a control signal can be applied to a multiplexer to govern whether an RDL flag associated with the byte under consideration will go to a state indicating the byte under consideration corresponds to the RDL character (e.g., high) or to a state indicating the byte under consideration does not correspond to the RDL character (e.g., low). Similar matching logic can be employed to test the AND operation output against the FDL character to yield an FDL flag associated with the byte under consideration. Furthermore, for embodiments where the DLF circuit is implemented in reconfigurable logic, the parallelism capabilities provided by the reconfigurable logic mean that the RDL character matching operation and the FDL character matching operation can be performed simultaneously.

Thus, the output of the DLF circuit shown by FIG. 14(a) will be a stream of outgoing bytes and their associated RDL and FDL flags.

Figure 14B:
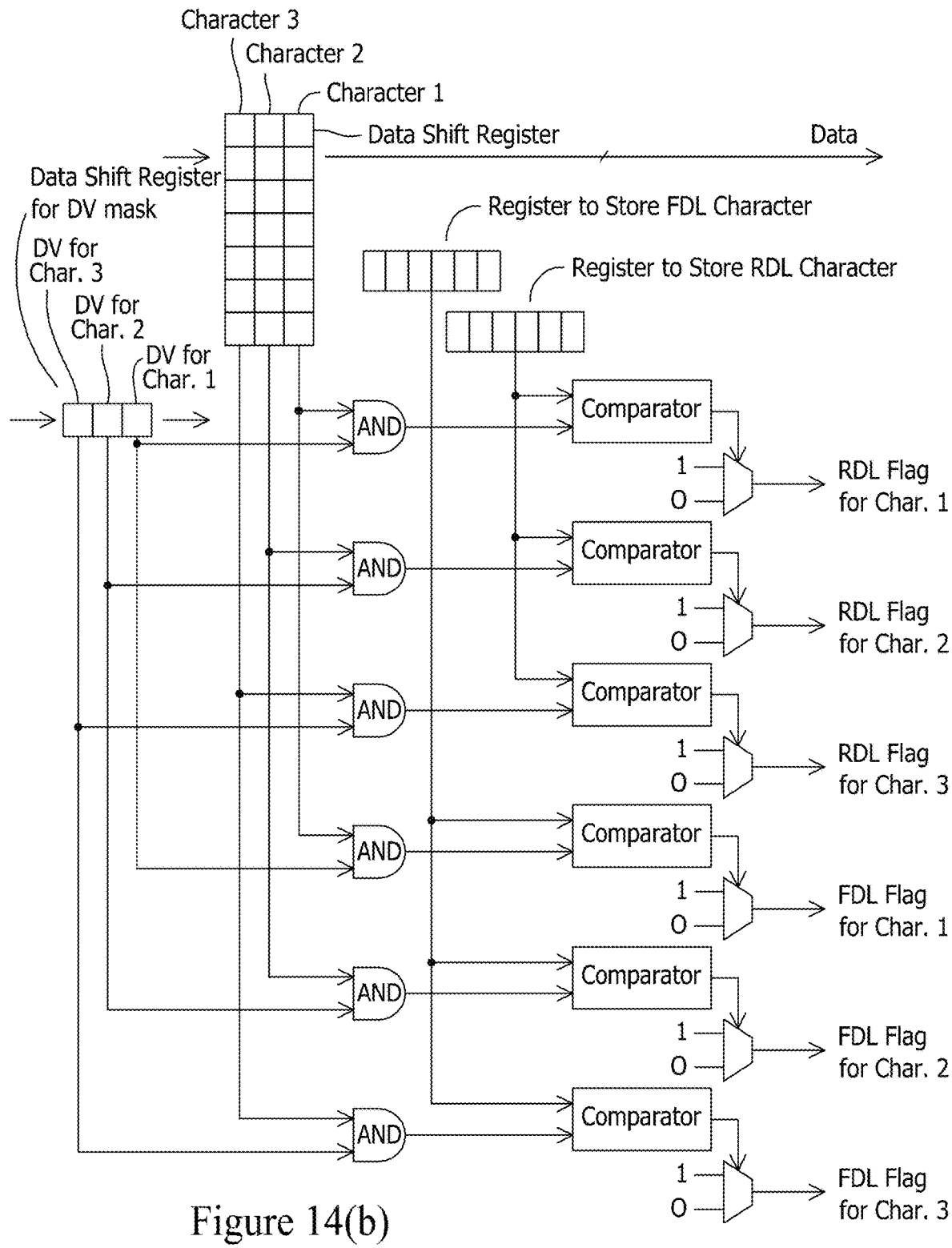

FIG. 14(b) depicts an example of a DLF circuit where the DLF circuit is configured to ingest multiple characters per clock cycle (e.g., 3 characters per clock cycle as shown in the example of FIG. 14(b)). Thus, the data shift register through which the byte stream is passed will have a multi-character data width (once again, a 3 character width in this example). Similarly, the data shift register through which the DV mask is passed will also have a data width that corresponds to the data width of the data shift register for the byte stream. Each clock cycle, the 3 characters of the data shift register and the DV masks corresponding to those three characters can be processed in parallel through replicated AND gates, comparators, and multiplexers to test the characters for matches against the RDL character and the FDL character. Upon completion of a cycle, the data shift registers can be configured to perform a shift by three characters to load the next set of characters for processing.

Figure 15:
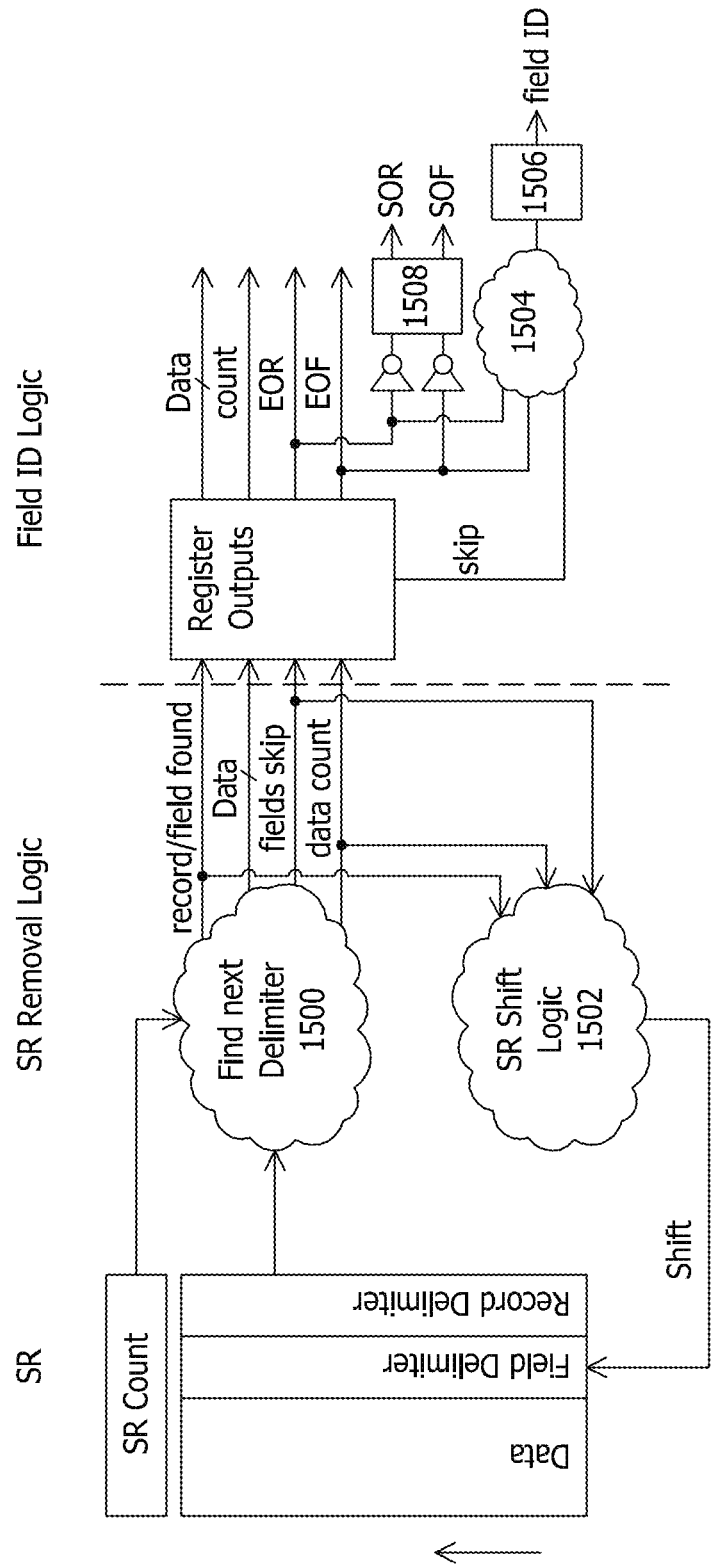
FIG. 15 depicts an exemplary shift register logic circuit and an exemplary field identifier logic circuit.

FIG. 15 provides additional detail regarding the SRL circuit and the FIDL circuit. The SRL circuit and the FIDL circuit can cooperate to pack the data headed downstream. FDL and RDL characters are removed from the byte stream, a count of skipped fields (e.g., empty fields) is generated, and the data characters that serve as field and record boundaries are marked. Further still, each field can be tagged with a field identifier for use by downstream processing. The output of the FIDL circuit can thus be the data characters of the byte stream and control data associated with those characters. This control data can take the form of a structured module chain interface (SMCI) protocol. The SMCI protocol can include a start of field (SOF) data, end of field (EOF) data, start of record (SOR) data, end of record (EOR) data, field identifier data, and count data, the count data being indicative of how many bytes should be consumed (e.g., how many bytes are valid in a transaction (transmission of a data word). For a data width of 8 bytes, for example, the count can range from 0-8 depending upon how many of the bytes are valid.

The SRL circuit of FIG. 15 can employ three shift registers—a data shift register through which the characters of the byte stream are pushed, a RDL shift register through which the RDL flag data is pushed, and a FDL shift register through which the FDL flag data is pushed. Logic 1500 can be configured to:
  Find the "leading" delimiter in the FDL or RDL register (the first character in the data register for which the corresponding FDL or RDL flag is high). The record/field found flag can be set as appropriate when a leading delimiter is found.
  Check the RDL and FDL flags following the leading delimiter to determine if an empty or skipped field/record is present. An empty/skipped field is a field with no data. Such an empty/skipped field appears in the byte stream as back to back FDL characters (as indicated by the FDL flag data). An empty/skipped record is a record with no data. Such an empty/skipped record appears in the byte stream as back to back RDL characters (as indicated by the RDL flag data).
  If there are back to back delimiters in the byte stream, determine a count of the empty fields/records and pull those off the shift register. This count is communicated as the Fields Skip output of the SRL circuit in FIG. 15.
  If non-empty fields are found, use the position of the delimiter (communicated as a bit in the field/record found register) to indicate how much data to pull off for the given field. This information can be communicated as the Data Count output of the SRL circuit in FIG. 15.

The shift logic 1502 can then operate in a fashion to cause the shift register to consume or strip off the delimiters. Thus, when delimiter characters are found in the byte stream based on the SMCI data, the shift logic 1502 can cause the shift register to shift out the delimiter characters while holding a data valid signal low. In this fashion, the delimiter characters are effectively dropped from the outgoing data stream.

The FIDL circuit then takes in the output of the SRL circuit in a register output and processes that output to generate an EOR flag and EOF flag for the data characters in the byte stream. Based on the delimiter following the data being pulled, the logic can determine whether to send an EOF or EOR marker (by checking the delimiter that triggered then end of the field/record). Logic 1504 and 1506 operate as a counter that increments the Field ID each time a new field in a record is encountered (in response to the skipped count, the EOR flag and the EOF flag). Thus, the Field ID can operate as an array index such that the first field has a Field ID of 0, the second field has a Field ID of 1, and so on. Furthermore logic 1508 operates to generate SOR and SOF flags from the EOR and EOF flags. The SOR/SOF/EOF/EOR data, count data, and Field ID data produced by the FIDL circuit can serve as the SMCI protocol control data associated with the outgoing bytes.

It should also be understood that the VRG module can be internally pipelined such that the QM circuit, the DLF circuit, the SRL circuit, and the FIDL circuit are configured to operate simultaneously in a pipelined fashion.

Figure 16:
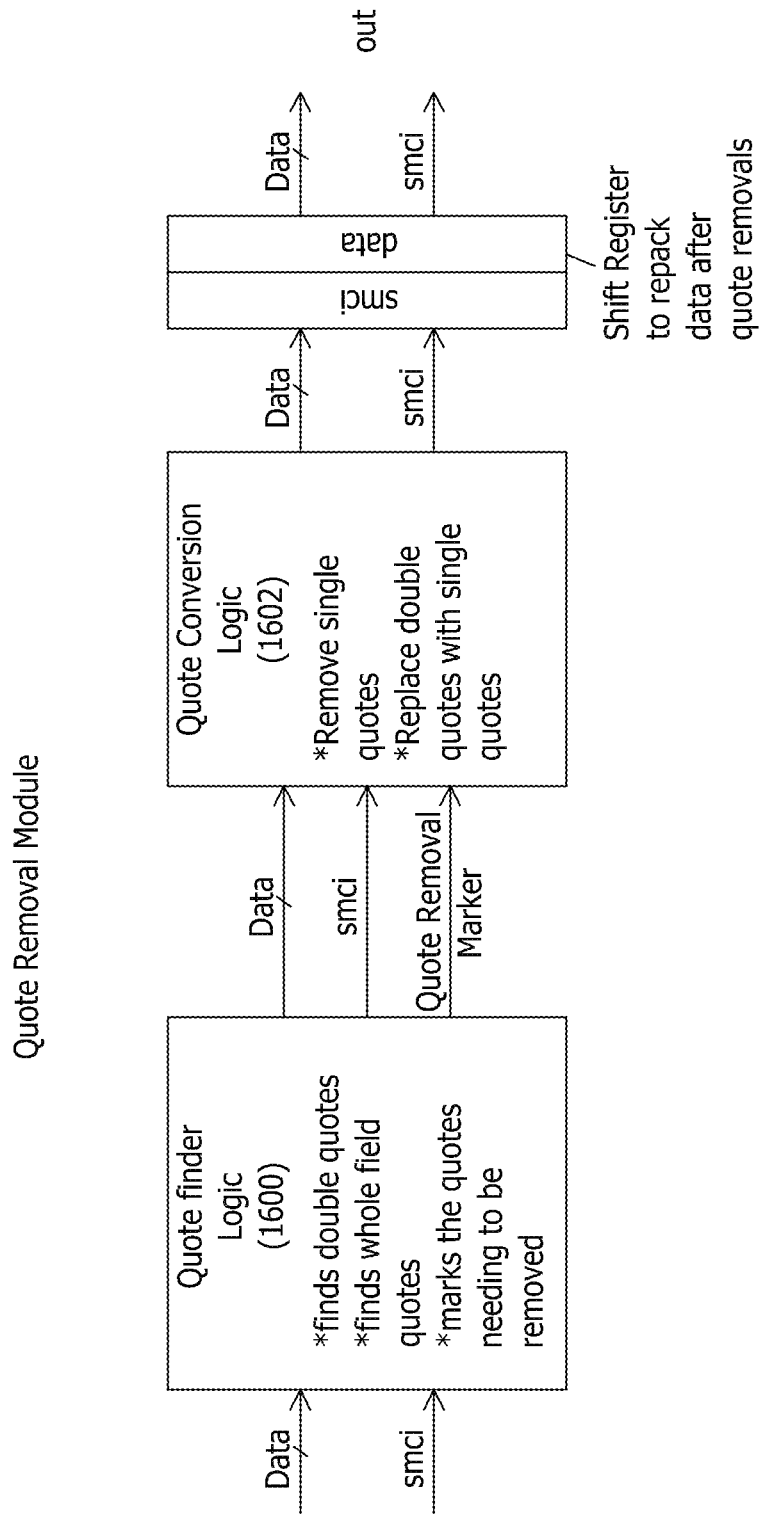
FIG. 16 depicts an exemplary quote removal (QRM) module.

QRM Module:

FIG. 16 depicts an exemplary arrangement for a QRM module. The QRM module is configured to strip the quotes used as the start and end of a field as shield characters and convert two consecutive quotes into a single quote.

The quote finder logic 1600 receives the data and SMCI signal from the VRG module output, and performs matching operations on the data to locate the characters that match the quote character. If a quote character in the data stream is at the start of a field (as indicated by the SOF flag in the SMCI control data), then the quote finder logic 1600 can mark that quote character for removal. If a quote character in the data stream is at the end of a field (as indicated by the EOF flag in the SMCI control data), then the quote finder logic 1600 can also mark that quote character for removal. Furthermore, if consecutive quote characters are found in the data stream, then the quote finder logic can mark the first quote for removal. Alternatively, the quote finder logic can be configured to merely mark the locations of quote characters in the data stream.

Thus, the quote finder logic 1600 provides the data stream, its associated SMCI control data, and the quote removal markers to quote conversion logic 1602. The quote conversion logic is configured to remove the single quotes from the data stream and replace the double quotes with single quotes. A shift register repacks the data from the quote conversion logic to accommodate the quote removals. Thus, the output of the shift register comprises the data stream and its corresponding SMCI control data.

The QRM module can also be internally pipelined such that the quote finder logic 1600, the quote conversion logic 1602 and shift register operate simultaneously in a pipelined fashion.

Figure 17A:
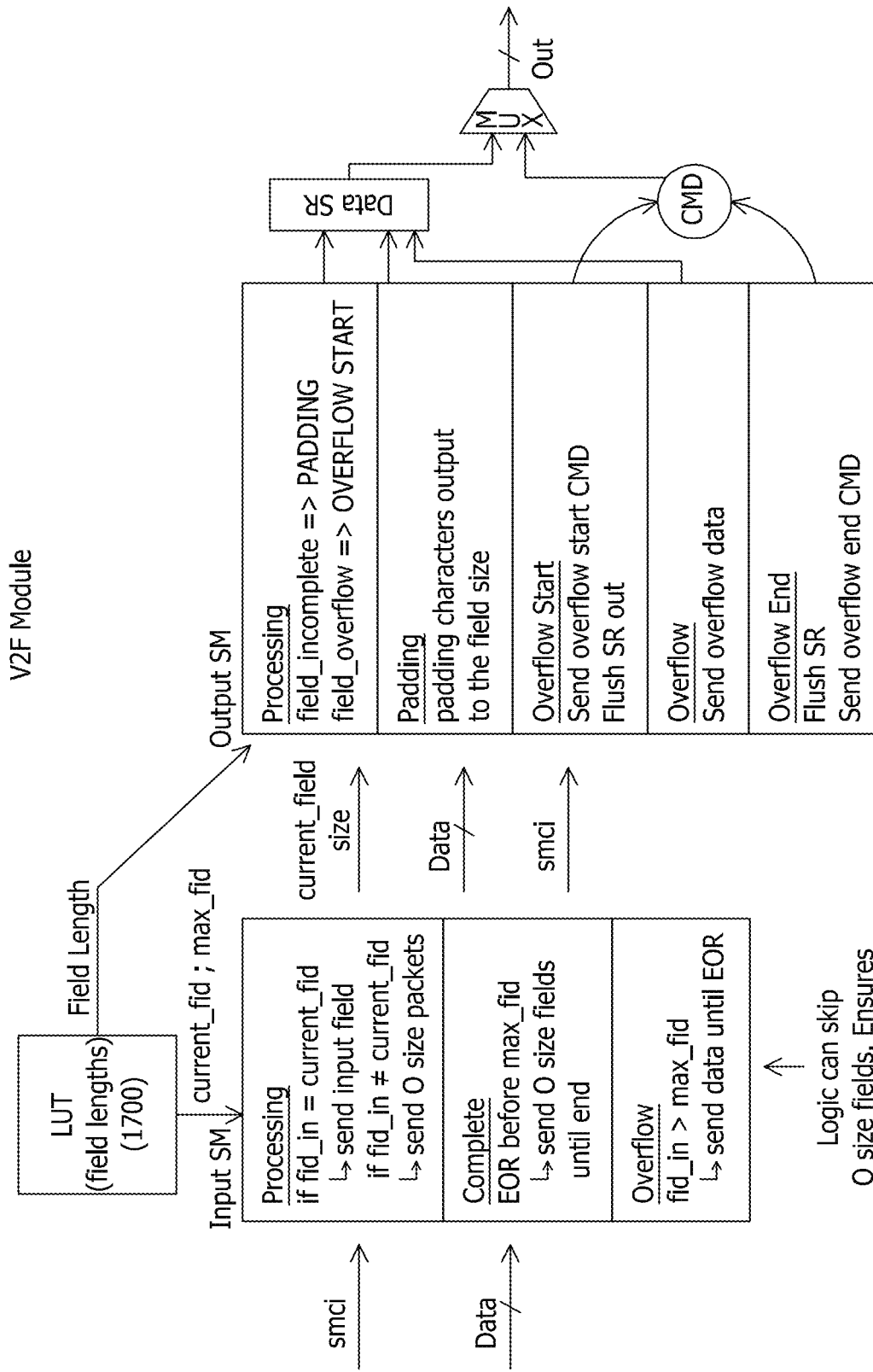
FIG. 17(a) depicts an exemplary variable-to-fixed (V2F) module.

V2F Module:

FIG. 17(a) depicts an exemplary arrangement for a V2F module. The V2F module can hold a map of field lengths to use for the fixed field format. The V2F module can use this map to fit the fields of the data stream to their appropriate length in accordance with the target fixed field format. The V2F module will pad out any field in the data stream shorter than the specification field length with a padding character, which can be a configurable special character. For ease of reference, these padding characters can be referred to as zeros for purposes of discussion. The V2F module will also output an overflow error for any field in the data stream longer than the specification field length.

The LUT stores a table of field widths that can be sent in from software. This table will thus have the length for each field as specified by software on startup. Thus, it should be understood that through these specified field lengths, each of the fields of the output fixed field formatted-data can have its own length that need not be the same length as the other fields. The index into this table represents the ID of a given field, and the value at that location represents the given field length. The last field identifier, and consequently the last populated field in the LUT, is stored in a last field identifier (max_fid) which is stored separately from the LUT. It is worth noting that some fields in this table can have a specified length of zero, meaning they are to be eliminated from output data records. (This can be used to eliminate fields that are generally not present in the input data.)

Figure 17B:
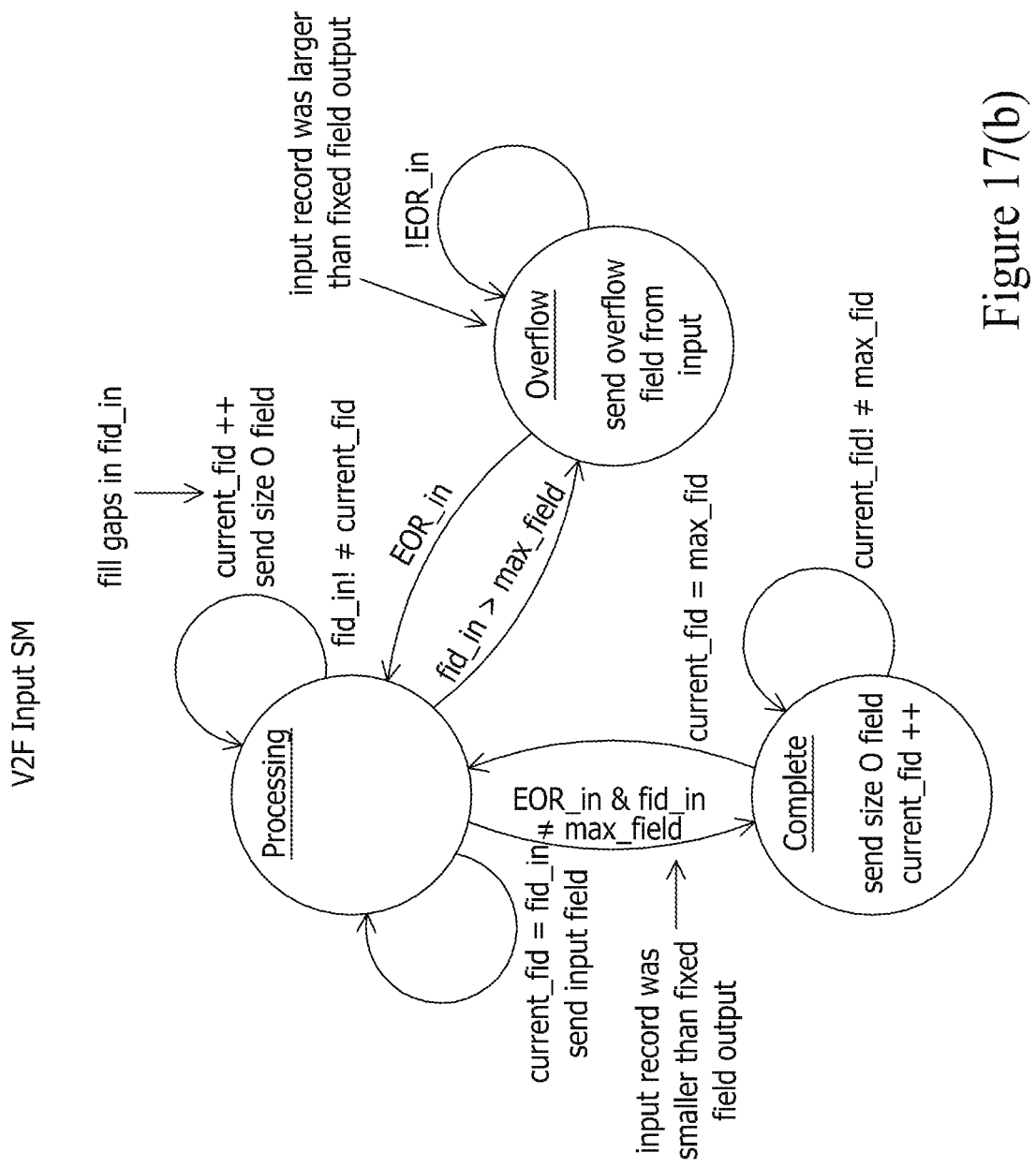
FIG. 17(b) depicts a state machine for the V2F module of FIG. 17(a).

An input state machine takes in the data stream and SMCI control data from the QRM module and compares it with the field identifiers from the LUT to reconcile the incoming fields with the expected fields for each record. The start of each field for the incoming data is marked in the SMCI data by the SOF flag while the end of each field is marked in the SMCI data by the EOF flag. Further still, the Field ID of the SMCI data will identify the field to which the current data of the data stream corresponds. From this information, the input state machine can transition between states of PROCESSING, COMPLETE, and OVERFLOW. FIG. 17(b) depicts an exemplary state machine diagram for the input state machine of FIG. 17(a).

In the PROCESSING state, if the field identifier for the incoming data (fid_in) matches the field identifier for the current field from the LUT (current_fid), then the incoming data can be sent to the output state machine for processing. However, while in the PROCESSING state, if fid_in does not match current_fid (and an EOR marker is not present), then this means that a gap in the incoming fields exists, and an empty field should be sent to the output state machine for processing. The next current_fid from the LUT is then processed.

If fid_in is greater than max_fid while the input state machine is in the PROCESSING state, the state machine transitions to the OVERFLOW state. This condition indicates that the input record included more fields than expected. While in the OVERFLOW state, the input state machine sends the overflow fields to the output state machine until an EOR marker is encountered in the incoming data. Upon encountering the EOR market in the incoming data, the input state machine will transition back to the PROCESSING state.

If_fid_in does not match max_fid and the EOR marker is present in the incoming data while the input state machine is in the PROCESSING state, this means that the incoming record had fewer fields than expected and we transition to the COMPLETE state. While in the COMPLETE state, the input state machine sends size zero fields to the output state machine and increments to the next current_fid from the LUT. Once current_fid reaches max_fid, the input state machine transitions back to the PROCESSING state.

The input state machine reports a data value indicative of the size of each identified field as it receives SOF markers from the input SMCI interface (current_field_size). For empty fields that are added to fill in a gap in a record, the current_field_size can be zero. For non-empty fields, a counter can be employed to identify how many bytes are present in each field (from the SOF and EOF markers in the SMCI control data associated with the incoming data).

The output state machine operates to fill fields with bytes of the incoming data or padding characters as necessary, and identify those fields which are overflowing with bytes of the incoming data as necessary. The output state machine can progress from a PROCESSING state (during which time the data stream fills the output data shift register that contains the output field) to a PADDING state (during which time padding characters are added to the output field) upon detection of a field incomplete condition. The field incomplete condition can occur if the current_field_size for an input field is less than the corresponding field length for the output field. Once the output field has been filled to the current_field_size, the output state machine can transition to the PADDING state.

While in the PADDING state, the remaining space in the output field is filled with padding characters until the padding characters added to the output field have caused the output field to reach the size of its field length. The output state machine can then return to the PROCESSING state.

The output state machine can also progress from the PROCESSING state to the OVERFLOW START state upon detection of a field overflow condition. The field overflow condition can occur if the current_field_size for an input field is greater than the corresponding field length for the output field. If this condition is detected, the output state machine can transition to the OVERFLOW START state. When in the OVERFLOW START state, an overflow start command (CMD) can be sent and the data shift register is flushed. The output state machine then progresses to the OVERFLOW state (during which time the overflow data is sent). Upon encountering the EOF flag for the overflowing field, the output state machine will progress to the OVERFLOW END state. During the OVERFLOW END state, an overflow end command (CMD) can be sent, and the shift register is flushed. Thus, overflowing fields are framed by overflow commands in the output data.

A command/data multiplexer is configured to provide either the CMDs from the output state machine or the content of the data shift register (SR) as an output. The state of the output state machine will govern which multiplexer input is passed as the multiplexer output. Thus, if the output state machine is in the OVERFLOW START or OVERFLOW END states, the multiplexer will pass command data indicative of these states to the output. While the output state machine is in the PROCESSING, PADDING, or OVERFLOW states, the multiplexer will pass the content of the output data shift register to the output. Accordingly, the V2F will output a fixed field of data when no overflows are detected. If an overflow is detected, a CMD signal frames the overflow data so that exception handling can further process the overflowing field.

Thus, the V2F module is able to deliver the data of the input byte stream 200 to the data processing stage 300 as a byte stream in a fixed field format.

Figure 18:
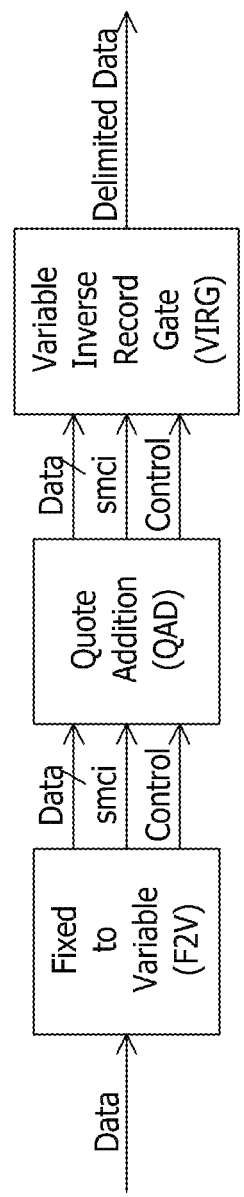
FIG. 18 depicts an exemplary pipeline that can be deployed by a translation engine to convert fixed field data to delimited data.

Translation Engine 400:

If it is desired to translate the processed data output of the data processing stage back to a delimited data format, the translation engine 400 can be configured with a pipeline of processing modules that effectively perform the inverse of the operations performed by the pipeline of FIG. 11. FIG. 18 depicts an exemplary pipeline that can be deployed by the translation engine 400. A fixed-to-variable (F2V) module can convert the incoming data in a fixed field format to the variable format having the SMCI control protocol. A quote addition (QAD) module downstream from the F2V module can insert shield characters into the data stream at appropriate locations as per the target delimited data format. A variable inverse record gate (VIRG) module downstream form the QAD module can insert FDL and RDL characters into the data stream at appropriate locations to thereby generate an output data stream in the target delimited data format.

Figure 19:
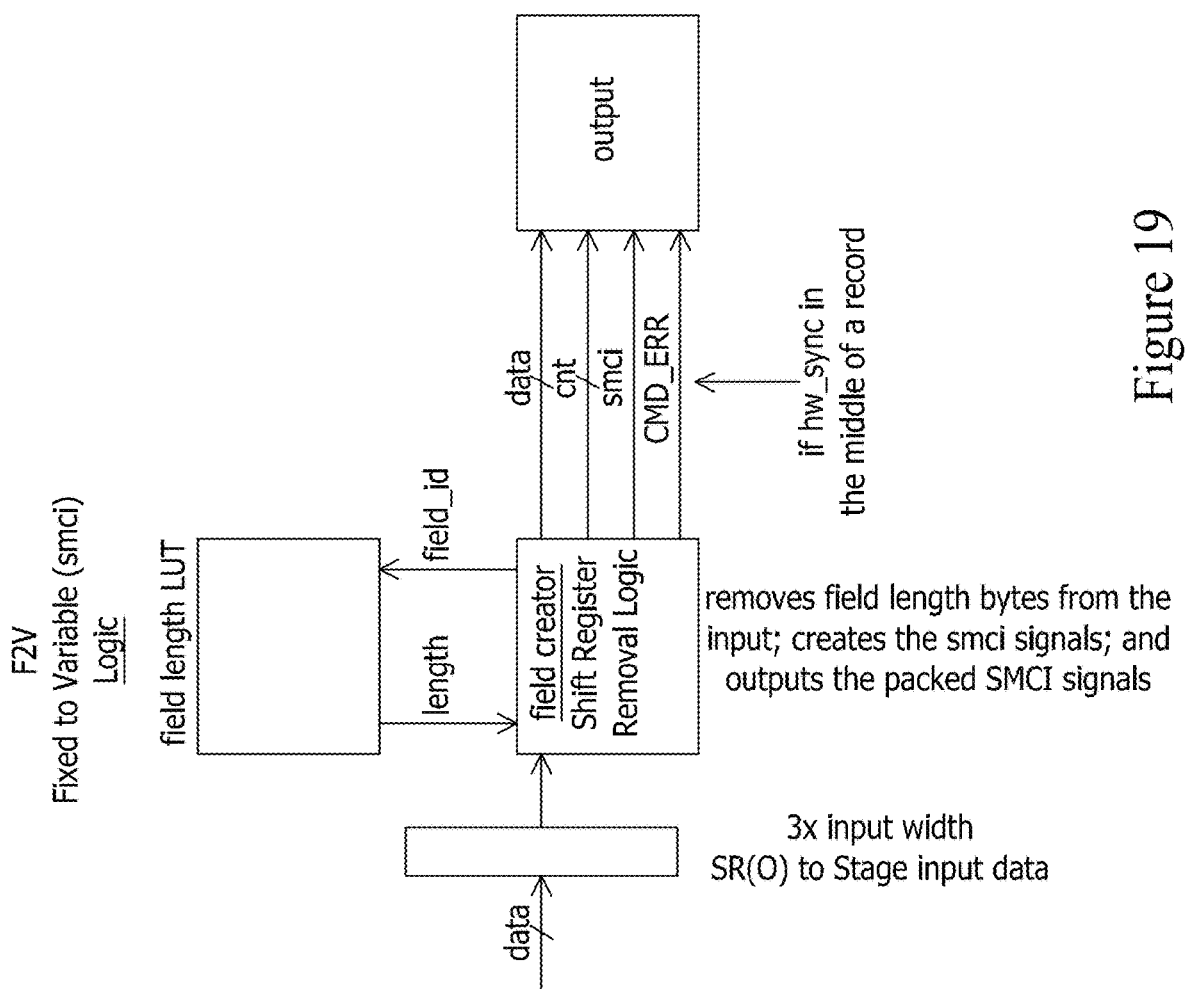
FIG. 19 depicts an exemplary fixed-to-variable (F2V) module.

FIG. 19 depicts an exemplary embodiment for the F2V module. Incoming data is shifted through a shift register, and a LUT of field lengths is used to ascertain the length of each incoming field. A field creator delineates the different fields of the incoming data and generates the associated SMCI control protocol data for those fields.

Figure 20:
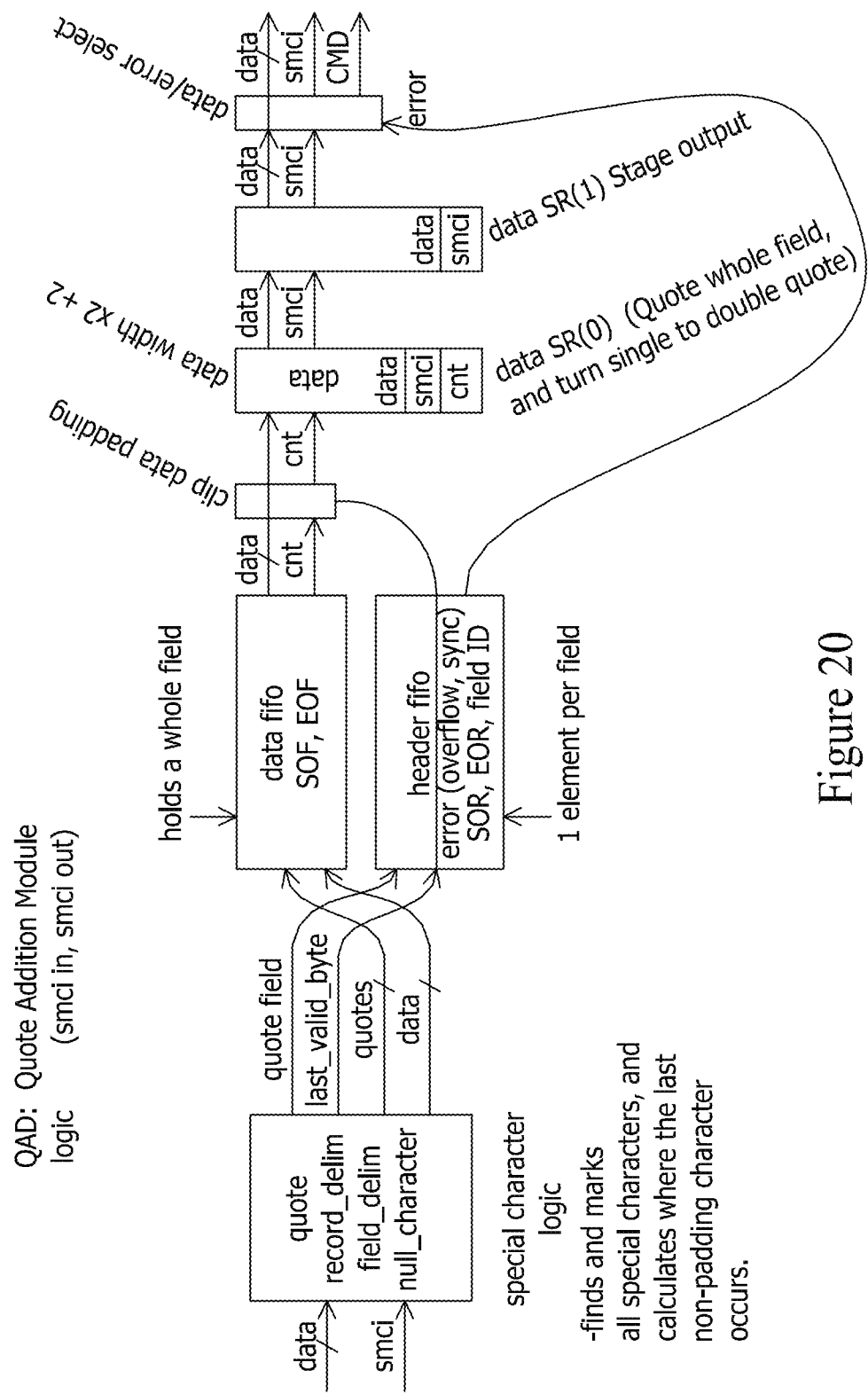
FIG. 20 depicts an exemplary quote addition (QAD) module.

FIG. 20 depicts an exemplary embodiment for the QAD module. The QAD module can inspect the incoming data for shield characters and delimiter characters to insert shield characters at appropriate locations as per the delimited data format. For example, if it detects a data character within a field that does not serve as an FDL character but matches the FDL character, the QAD module will operate to wrap that field with quote marks. The QAD module can also operate to strip the incoming data of padding characters that may have been added to the fields to fillout the fixed fields. A special character logic in the QAD module can operate to detect and mark all special characters (shield characters, FDL characters, and RDL characters) in the data stream for populating the data and header queues. A padding clipper that then culls the data stream of padding characters and shift registers can be employed to repack the outgoing data.

Figure 21:
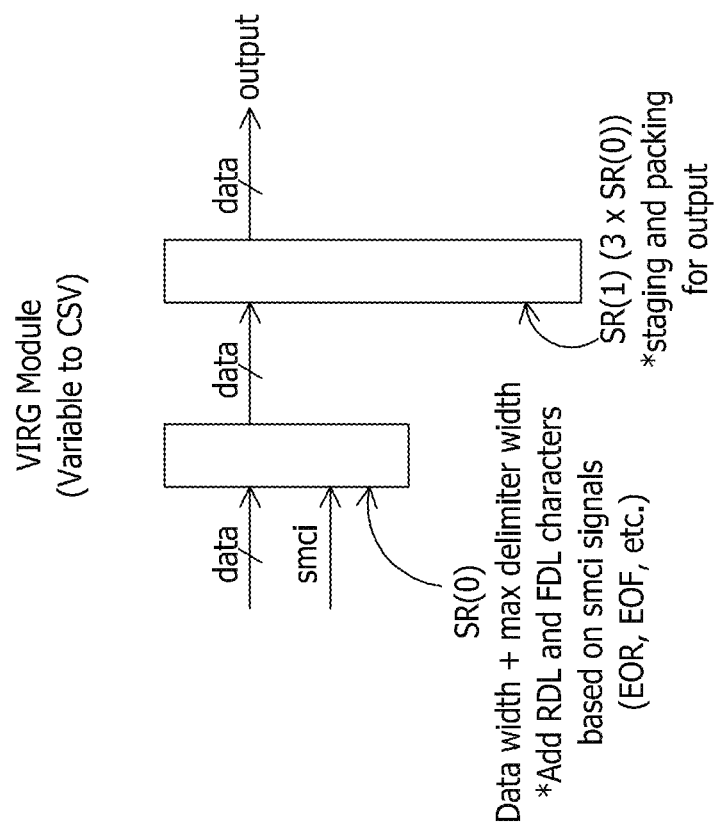
FIG. 21 depicts an exemplary variable inverse record gate (VIRG) module.

FIG. 21 depicts an exemplary VIRG module. The VIRG module can take in the data output from the QAD module together with the associated SMCI control data to insert actual RDL characters and FDL characters at appropriate locations in the data stream via processing logic triggered by the SMCI control data and corresponding shift registers. Thus, the output of the VIRG module will be a stream of data in the delimited data format.

Selective Enabling and Disabling of Engines and Processing Modules:

It should also be understood that command data can be inserted into the data stream to enable and disable various modules of the processing pipeline deployed by the translation engine(s) as appropriate for a processing task. For example, in an embodiment where both translation engine 202 and translation engine 400 are employed (for example in reconfigurable logic), and if the destination for the delimited data is a database, a practitioner may choose to disable the translation engine 400. The disabled translation engine 400 would thus act as a pass through while remaining instantiated on the reconfigurable logic. As another example, if the incoming delimited data does not include shield characters, command data can be employed to disable the QM circuit of the VRG module and the QRM module. Such disabled modules would thus act as pass through components while remaining instantiated on the reconfigurable logic.

Figure 22:
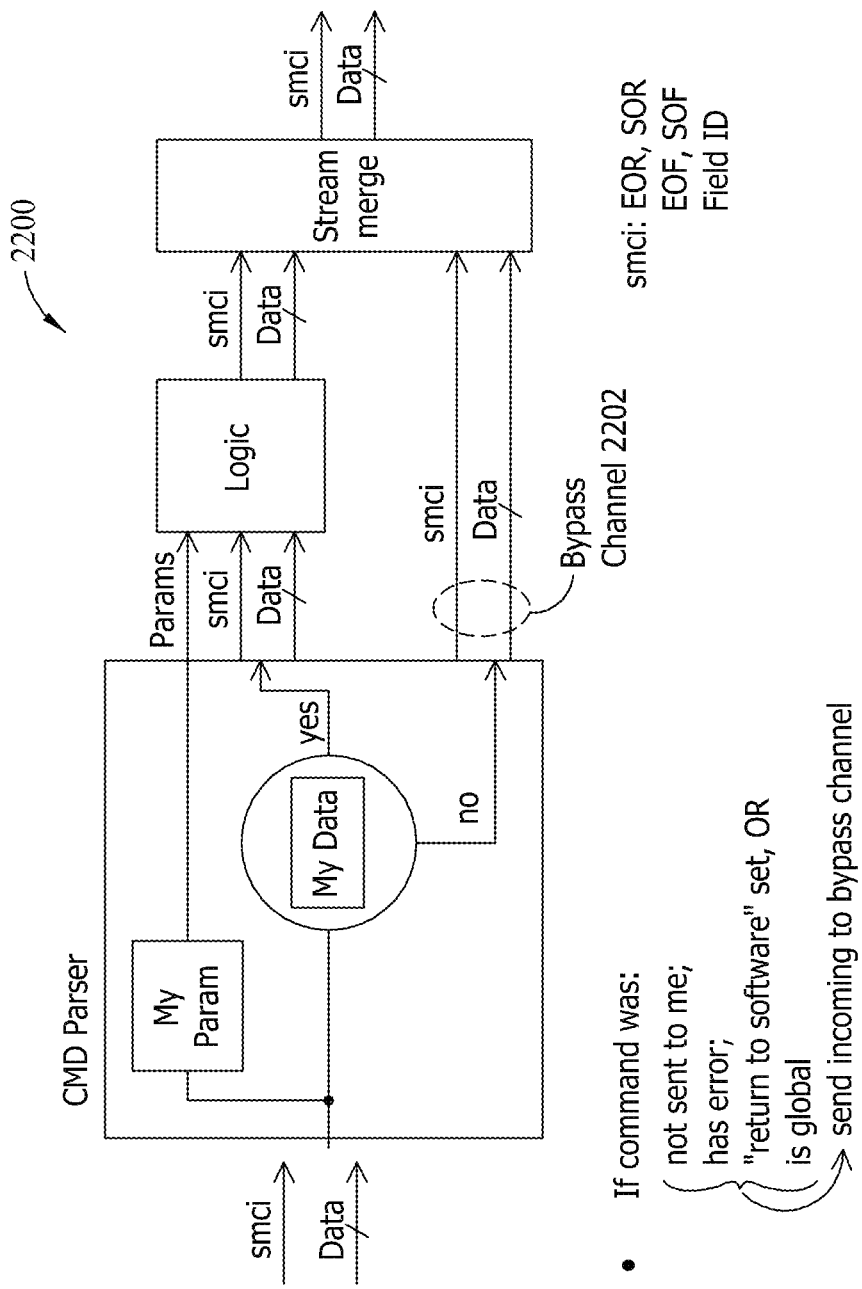
FIG. 22 depicts an exemplary arrangement for a processing module, where the processing module includes a bypass path and a processing path.

FIG. 22 depicts an exemplary arrangement for a processing module to support a selective enabling/disabling functionality. The module 2200 of FIG. 22 can include a command parser block, a logic block downstream from the command parser block, and a stream merge block downstream from the command parser block and the logic block.

The command parser block operates to receive the incoming data stream (which in this example is incoming data and associated SMCI control protocol; however, this need not be the case) and interpret the content of that stream to determine whether the incoming data is to be processed by the logic block or to bypass the logic block. Two criteria can determine whether data or commands will be processed by a module. For commands specifically, a module ID is present in a command to denote which specific module the command targets. There can be a special case for a module ID of zero that denotes the command applies to the entire chain. In addition to command routing, a context identifier can be used to denote which stream of data is currently being processed. Different modules can be bound to different contexts or streams.

Command messages are used to toggle the "plumbing" of a given module chain, turning modules ON or OFF (pass through) for a given context, and are used to mark changes in the active context. As a result, commands are sent through to set up the active data routes for a context and are used to denote which context is active. After the command setup, data will be processed by that configured chain until new commands arrive to enable/disable modules or toggle a context switch.

The command parser is responsible for inspecting command headers to note whether or not the command is intended for the given module, and it is responsible for following context switching commands that denote the active context.

When the module is in pass through, or is observing data from a context for which it is not bound, all data will be sent through the bypass channel 2202 rather than through the logic block. To disable an entire engine (such as translation engine 400), all of the modules that make up that engine can be disabled.

The logic block can implement any of the processing tasks described herein for the translation engine (e.g., the VRG module, the QM circuit, the V2F module, etc.).

The stream merge block operates to merge the output of the logic block and the information on the bypass channel to generate an output from the module. Data from the bypass channel will be given precedence over data from the logic block (if both are available), and the stream merge block is responsible for ensuring that data and commands are merged in on proper data boundaries.

The exemplary embodiments described herein can be used for a wide array of data processing tasks where performing data translations at low latency and high throughput are desired. Any enterprise in which data in a delimited format is widely used as the mode of communicating data records from location to location is expected to greatly benefit from use of the disclosed embodiments. For example, medical records and health care data are often communicated via a delimited data format and would benefit from improvements in how such data is processed (particularly in connection with data quality checking operations and database ETL operations).

While the present invention has been described above in relation to its exemplary embodiments, various modifications may be made thereto that still fall within the invention's scope. Such modifications to the invention will be recognizable upon review of the teachings herein. Accordingly, the full scope of the present invention is to be defined by the appended claims and their legal equivalents.

What is claimed is:

1. A method for low latency and high throughput data translation, the method comprising:

receiving, by a pipeline, an incoming stream comprising a plurality of bytes arranged in a delimited data format, the incoming byte stream being representative of data arranged in a plurality of fields, the incoming byte stream comprising a plurality of data characters, a plurality of shield characters, and a plurality of field delimiter characters, the field delimiter characters defining a plurality of boundaries between the fields, wherein the pipeline is deployed on at least one of (1) a reconfigurable logic device, (2) a graphics processor unit (GPU), (3) an application-specific integrated circuit (ASIC), and/or (4) a chip multi-processor (CMP);

the pipeline processing the bytes of the received byte stream as the bytes stream through the pipeline, wherein the processing step includes the pipeline translating the received byte stream to an outgoing byte stream arranged in a fixed field format, the outgoing byte stream comprising a plurality of the data characters of the received byte stream arranged in a plurality of fixed-size fields and stripped of the field delimiter characters and the shield characters;

wherein the processing step comprises the pipeline repeatedly performing a shield character masking step and a field delimiter finding step in parallel and in a pipelined manner as the bytes stream through the pipeline to create the outgoing byte stream;

wherein the shield character masking step comprises the pipeline generating a shield character mask based on the shield characters in the received byte stream, wherein the shield character mask distinguishes between bytes in the received byte stream that may include field delimiter characters and bytes in the received byte stream that do not include field delimiter characters; and wherein the field delimiter finding step comprises the pipeline identifying the field delimiter characters in the received byte stream based on the shield character mask.

2. The method of claim 1 wherein the field delimiter finding step further comprises the pipeline tracking locations in the received byte stream corresponding to the identified field delimiter characters.

3. The method of claim 2 wherein the field delimiter finding step further comprises the pipeline stripping the identified field delimiter characters from the received byte stream.

4. The method of claim 2 wherein the processing step further comprises the pipeline repeatedly performing the shield character masking step, the field delimiter finding step, a shield character removing step, and a fixed field arranging step in parallel and in the pipelined manner as the bytes stream through the pipeline to create the outgoing byte stream;

wherein the shield character removing step comprises the pipeline (1) distinguishing between (i) the shield characters in the received byte stream and (ii) data characters in the received byte stream that happen to match the shield character to thereby identify the shield characters in the received byte stream, and (2) removing the identified shield characters from the received byte stream; and wherein the fixed field arranging step comprises the pipeline arranging the data characters of the received byte stream into the fixed-size fields based on the tracked locations of the identified field delimiter characters to thereby create the outgoing byte stream.

5. The method of claim 1 wherein the incoming byte stream comprises a plurality of records in the delimited data format, each record comprising data arranged in at least one of the fields, the incoming byte stream further comprising a plurality of record delimiter characters, the record delimiter characters defining a plurality of boundaries between the records;

wherein the outgoing byte stream comprises the records of the incoming byte stream arranged in the fixed field format, wherein the data characters of the received byte stream are arranged in the fixed-size fields and stripped of the field delimiter characters, the record delimiter characters, and the shield characters;

wherein the shield character mask distinguishes between bytes in the received byte stream that may include field delimiter characters and/or record delimiter characters and bytes in the received byte stream that do not include field delimiter characters or record delimiter characters; and wherein the field delimiter finding step is part of a delimiter finding step that also comprises the pipeline identifying the record delimiter characters in the received byte stream based on the shield character mask.

6. The method of claim 1 further comprising:
a computer system selectively targeting a field of the outgoing byte stream for processing without analyzing the data characters of the outgoing byte stream.

7. The method of claim 6 further comprising:
the computer system performing a field-specific data processing operation on the selectively targeted field of the outgoing byte stream.

8. The method of claim 7 wherein the field-specific data processing operation comprises a data quality checking operation as part of an extract, transfer, load (ETL) procedure.

9. The method of claim 1 wherein the pipeline is deployed on a reconfigurable logic device.

10. The method of claim 1 wherein the pipeline is deployed on a GPU.

11. The method of claim 1 wherein the processing step comprises the pipeline performing the processing step on a plurality of bytes of the received byte stream per clock cycle.

12. The method of claim 1 wherein the delimited data format is a comma separated value (CSV) format.

13. The method of claim 1 wherein the step of generating the shield character mask comprises:
the pipeline processing the byte stream through a state machine that includes (1) a first state that will mark the shield character mask to identify a byte as a candidate to be a field delimiter and (2) a second state that will mark the shield character mask to identify a byte as not a candidate to be a field delimiter;

the pipeline controllably transitioning between the first state and the second state for the bytes of the byte stream based on a detection for each byte in the byte stream as to whether it matches the shield character; and the pipeline producing the shield character mask as the bytes are processed through the state machine.

14. The method of claim 13 wherein the controllably transitioning step comprises the pipeline toggling between the first and second states on each detection of a byte in the byte stream that matches the shield character.

15. The method of claim 13 further comprising:
the pipeline associating bytes of the byte stream with corresponding portions of the shield character mask, and wherein the shield character mask portions comprise a plurality of flags that indicate whether their associated bytes in the byte stream are candidates to be a field delimiter.

16. The method of claim 15 wherein the field delimiter finding step comprises:
the pipeline determining which bytes of the byte stream are candidates to be a field delimiter based on their corresponding flags in shield character mask;

the pipeline comparing the bytes determined to be field delimiter candidates with the field delimiter character to determine whether there is a match; and the pipeline identifying the field delimiter characters based on matches found by the comparing step.

17. The method of claim 16 wherein the step of determining which bytes of the byte stream are candidates to be a field delimiter based on their corresponding flags in shield character mask comprises combining the bytes of the byte stream with their corresponding flags in the shield character mask via combinatorial AND logic.

18. The method of claim 1 further comprising:
the pipeline associating bytes of the byte stream with corresponding portions of the shield character mask, wherein the shield character mask portions comprise a plurality of flags that indicate whether their associated bytes in the byte stream are candidates to be a field delimiter.

19. The method of claim 18 wherein the field delimiter finding step comprises:
the pipeline determining which bytes of the byte stream are candidates to be a field delimiter based on their corresponding flags in shield character mask;
the pipeline comparing the bytes determined to be field delimiter candidates with the field delimiter character to determine whether there is a match; and
the pipeline identifying the field delimiter characters based on matches found by the comparing step.

20. The method of claim 18 wherein the step of generating the shield character mask comprises processing the byte stream through a state machine to produce the flags for the shield character mask.

21. An apparatus for low latency and high throughput data translation, the apparatus comprising:
at least one of (1) a reconfigurable logic device, (2) a graphics processor unit (GPU), (3) an application-specific integrated circuit (ASIC), and/or (4) a chip multi-processor (CMP) on which a pipeline is deployed;
wherein the pipeline is configured to receive an incoming stream comprising a plurality of bytes arranged in a delimited data format, the incoming byte stream being representative of data arranged in a plurality of fields, the incoming byte stream comprising a plurality of data characters, a plurality of shield characters, and a plurality of field delimiter characters, wherein the field delimiter characters define a plurality of boundaries between the fields;
wherein the pipeline is further configured to process the bytes of the received byte stream as the bytes stream through the pipeline to translate the received byte stream to an outgoing byte stream arranged in a fixed field format, the outgoing byte stream comprising a plurality of the data characters of the received byte stream arranged in a plurality of fixed-size fields and stripped of the field delimiter characters and the shield characters;
wherein the pipeline comprises a plurality of processing modules that are configured to operate in parallel and in a pipelined manner to create the outgoing byte stream as the bytes stream through the pipeline, wherein the processing modules comprise a first processing module and a second processing module;
wherein the first processing module is configured to generate a shield character mask based on the shield characters in the received byte stream, wherein the shield character mask distinguishes between bytes in the received byte stream that may include field delimiter characters and bytes in the received byte stream that do not include field delimiter characters; and
wherein the second processing module is configured to identify the field delimiter characters in the received byte stream based on the shield character mask.

22. The apparatus of claim 21 wherein the second processing module is further configured to track locations in the received byte stream corresponding to the identified field delimiter characters.

23. The apparatus of claim 22 wherein the second processing module is further configured to strip the identified field delimiter characters from the received byte stream.

24. The apparatus of claim 22 wherein the processing modules further comprise a third processing module and a fourth processing module;
wherein the third processing module is configured to (1) distinguish between (i) the shield characters in the received byte stream and (ii) data characters in the received byte stream that happen to match the shield character to thereby identify the shield characters in the received byte stream, and (2) remove the identified shield characters from the received byte stream; and
wherein the third processing module is configured to arrange the data characters of the received byte stream into the fixed-size fields based on the tracked locations of the identified field delimiter characters to thereby create the outgoing byte stream.

25. The apparatus of claim 21 wherein the incoming byte stream comprises a plurality of records in the delimited data format, each record comprising data arranged in at least one of the fields, the incoming byte stream further comprising a plurality of record delimiter characters, wherein the record delimiter characters define a plurality of boundaries between the records;
wherein the outgoing byte stream comprises the records of the incoming byte stream arranged in the fixed field format, wherein the data characters of the received byte stream are arranged in the fixed-size fields and stripped of the field delimiter characters, the record delimiter characters, and the shield characters;
wherein the shield character mask distinguishes between bytes in the received byte stream that may include field delimiter characters and/or record delimiter characters and bytes in the received byte stream that do not include field delimiter characters or record delimiter characters; and
wherein the second processing module is further configured to identify the record delimiter characters in the received byte stream based on the shield character mask.

26. The apparatus of claim 21 further comprising:
another processor that is configured to selectively target a field of the outgoing byte stream for processing without analyzing the data characters of the outgoing byte stream.

27. The apparatus of claim 26 wherein the another processor is further configured to perform a field-specific data processing operation on the selectively targeted field of the outgoing byte stream.

28. The apparatus of claim 27 wherein the field-specific data processing operation comprises a data quality checking operation as part of an extract, transfer, load (ETL) procedure.

29. The apparatus of claim 21 wherein the pipeline is deployed on a reconfigurable logic device.

30. The apparatus of claim 21 wherein the pipeline is deployed on a GPU.

31. The apparatus of claim 21 wherein the pipeline is further configured to process a plurality of bytes of the received byte stream per clock cycle.

32. The apparatus of claim 21 wherein the delimited data format is a comma separated value (CSV) format.

33. The apparatus of claim 21 wherein the first processing module comprises a state machine that includes (1) a first state that will mark the shield character mask to identify a byte as a candidate to be a field delimiter and (2) a second state that will mark the shield character mask to identify a byte as not a candidate to be a field delimiter;
wherein the state machine is configured to process the bytes of the byte stream and controllably transition between the first state and the second state for the processed bytes of the byte stream based on a detection for each byte in the byte stream as to whether it matches the shield character; and
wherein the state machine is further configured to produce the shield character mask as the bytes are processed therethrough.

34. The apparatus of claim 33 wherein the state machine is further configured to controllably transition between the first and second states by toggling between the first and second states on each detection of a byte in the byte stream that matches the shield character.

35. The apparatus of claim 33 wherein the pipeline is further configured to associate bytes of the byte stream with corresponding portions of the shield character mask, and wherein the shield character mask portions comprise a plurality of flags that indicate whether their associated bytes in the byte stream are candidates to be a field delimiter.

36. The apparatus of claim 35 wherein the second processing module is further configured to:
determine which bytes of the byte stream are candidates to be a field delimiter based on their corresponding flags in shield character mask;
compare the bytes determined to be field delimiter candidates with the field delimiter character to determine whether there is a match; and
identify the field delimiter characters based on matches found by the comparisons.

37. The apparatus of claim 36 wherein the second processing module comprises combinatorial AND logic that combines the bytes of the byte stream with their corresponding flags in the shield character mask to determine which bytes of the byte stream are candidates to be a field delimiter.

38. The apparatus of claim 21 wherein the pipeline is further configured to associate bytes of the byte stream with corresponding portions of the shield character mask, wherein the shield character mask portions comprise a plurality of flags that indicate whether their associated bytes in the byte stream are candidates to be a field delimiter.

39. The apparatus of claim 38 wherein the second processing module is further configured to:
determine which bytes of the byte stream are candidates to be a field delimiter based on their corresponding flags in shield character mask;
compare the bytes determined to be field delimiter candidates with the field delimiter character to determine whether there is a match; and
identify the field delimiter characters based on matches found by the comparisons.

40. The apparatus of claim 38 wherein the first processing module comprises a state machine that processes the byte stream to produce the flags for the shield character mask.

* * * * *